(12) United States Patent
Sommerich et al.

(10) Patent No.: US 8,241,294 B2
(45) Date of Patent: Aug. 14, 2012

(54) INSTRUMENTS FOR EXPANDABLE CORPECTOMY SPINAL FUSION CAGE

(75) Inventors: Robert Sommerich, Norton, MA (US); Glen Arthur Presbrey, Mapleville, RI (US); Martin Meer, Vohringen (DE); Gerhard Pohl, Sankt Georgen (DE); Katherine Herard, Harrisville, RI (US)

(73) Assignee: DePuy Spine, Inc., Raynham, MA (US)

( * ) Notice: Subject to any disclaimer, the term of this patent is extended or adjusted under 35 U.S.C. 154(b) by 295 days.

(21) Appl. No.: 12/055,805

(22) Filed: Mar. 26, 2008

(65) Prior Publication Data

US 2009/0164018 A1    Jun. 25, 2009

Related U.S. Application Data

(63) Continuation of application No. 11/960,623, filed on Dec. 19, 2007.

(51) Int. Cl.
*A61B 17/58* (2006.01)

(52) U.S. Cl. ......... 606/90; 606/99; 606/86 A; 623/17.11

(58) Field of Classification Search .... 623/17.11–17.16; 606/99, 86 A, 86 B, 90
See application file for complete search history.

(56) References Cited

U.S. PATENT DOCUMENTS

| | | | |
|---|---|---|---|
| 4,657,550 A | 4/1987 | Daher |
| 4,911,718 A | 3/1990 | Lee |
| 4,961,740 A | 10/1990 | Ray |
| 5,026,373 A | 6/1991 | Ray |
| 5,122,130 A | 6/1992 | Keller |
| 5,171,281 A | 12/1992 | Parsons |
| 5,236,460 A | 8/1993 | Barber |
| 5,290,312 A | 3/1994 | Kojimoto |
| 5,458,641 A | 10/1995 | Ramirez Jimenez |
| 5,510,370 A | 4/1996 | Hock |
| 5,545,229 A | 8/1996 | Parsons |
| 5,571,190 A | 11/1996 | Ulrich |
| 5,571,192 A | 11/1996 | Schonhoffer |
| 5,658,335 A | 8/1997 | Allen |
| 5,683,408 A | 11/1997 | De Laage De Meux et al. |
| 5,702,451 A | 12/1997 | Biedermann |
| 5,702,453 A | 12/1997 | Rabbe |
| 5,702,455 A | 12/1997 | Saggar |
| 5,723,013 A | 3/1998 | Jeanson |
| 5,776,197 A | 7/1998 | Rabbe |
| 5,776,198 A | 7/1998 | Rabbe |
| 5,827,328 A | 10/1998 | Buttermann |

(Continued)

FOREIGN PATENT DOCUMENTS

EP    968692    1/2000

(Continued)

OTHER PUBLICATIONS

Russegger, "First Experiences With A Distractible Titanium Implant In Vvntral Cervical Disc Surgery: Report On 30 Consecutive Cases", *Eur Spine J*, 1997; 6(1), pp. 70-73.

(Continued)

*Primary Examiner* — Eduardo C Robert
*Assistant Examiner* — Julianna N Harvey

(57) ABSTRACT

An instrument set for an intervertebral expandable spacer having a pair of co-axial annuluses locked together by an engagement member, the set including an inserter/expander having both a rapid expansion mechanism and a fine tuning expansion mechanism.

4 Claims, 28 Drawing Sheets

U.S. PATENT DOCUMENTS

| | | |
|---|---|---|
| 5,856,138 A | 1/1999 | Fukuda |
| 5,860,977 A | 1/1999 | Zucherman |
| 5,876,404 A | 3/1999 | Zucherman |
| 5,916,267 A | 6/1999 | Tienboon |
| 5,972,031 A | 10/1999 | Biedermann |
| 5,989,290 A | 11/1999 | Biedermann |
| 6,015,436 A | 1/2000 | Schonhoffer |
| 6,048,342 A | 4/2000 | Zucherman |
| 6,049,026 A | 4/2000 | Muschler |
| 6,066,175 A | 5/2000 | Henderson |
| 6,068,630 A | 5/2000 | Zucherman |
| 6,074,390 A | 6/2000 | Zucherman |
| 6,080,193 A | 6/2000 | Hochshuler |
| 6,086,613 A | 7/2000 | Camino |
| 6,090,112 A | 7/2000 | Zucherman |
| 6,126,660 A | 10/2000 | Dietz |
| 6,149,652 A | 11/2000 | Zucherman |
| 6,152,926 A | 11/2000 | Zucherman |
| 6,156,038 A | 12/2000 | Zucherman |
| 6,174,334 B1 | 1/2001 | Suddaby |
| 6,176,881 B1 | 1/2001 | Schär et al. |
| 6,183,471 B1 | 2/2001 | Zucherman |
| 6,190,387 B1 | 2/2001 | Zucherman |
| 6,190,413 B1 | 2/2001 | Sutcliffe |
| 6,193,755 B1 | 2/2001 | Metz Stavenhagen |
| 6,193,756 B1 | 2/2001 | Studer |
| 6,200,348 B1 | 3/2001 | Biedermann |
| 6,235,030 B1 | 5/2001 | Zucherman |
| 6,238,397 B1 | 5/2001 | Zucherman |
| 6,261,296 B1 | 7/2001 | Aebi et al. |
| 6,280,444 B1 | 8/2001 | Zucherman |
| 6,296,647 B1 | 10/2001 | Robioneck |
| 6,299,644 B1 | 10/2001 | Vanderschot |
| 6,319,257 B1 | 11/2001 | Carignan |
| 6,332,882 B1 | 12/2001 | Zucherman |
| 6,332,883 B1 | 12/2001 | Zucherman |
| 6,332,895 B1 | 12/2001 | Suddaby |
| 6,344,057 B1 | 2/2002 | Rabbe |
| 6,352,556 B1 | 3/2002 | Kretschmer |
| 6,375,681 B1 | 4/2002 | Truscott |
| 6,379,355 B1 | 4/2002 | Zucherman |
| 6,419,676 B1 | 7/2002 | Zucherman |
| 6,419,677 B2 | 7/2002 | Zucherman |
| 6,419,705 B1 | 7/2002 | Erickson |
| 6,451,020 B1 | 9/2002 | Zucherman |
| 6,454,806 B1 | 9/2002 | Cohen |
| 6,478,796 B2 | 11/2002 | Zucherman |
| 6,500,178 B2 | 12/2002 | Zucherman |
| 6,514,256 B2 | 2/2003 | Zucherman |
| 6,524,341 B2 | 2/2003 | Läng |
| 6,527,803 B1 | 3/2003 | Crozet |
| 6,562,074 B2 | 5/2003 | Gerbec |
| 6,590,081 B1 | 7/2003 | Zhang |
| 6,616,695 B1 | 9/2003 | Crozet |
| 6,660,038 B2 | 12/2003 | Boyer, II |
| 6,712,825 B2 | 3/2004 | Aebi |
| 6,716,218 B2 | 4/2004 | Holmes |
| 6,730,088 B2 | 5/2004 | Yeh |
| 6,752,832 B2 | 6/2004 | Neumann |
| 6,758,862 B2 | 7/2004 | Berry |
| 6,776,197 B1 | 8/2004 | DeCrane |
| 6,776,798 B2 | 8/2004 | Camino |
| 6,805,714 B2 | 10/2004 | Sutcliffe |
| 6,808,538 B2 | 10/2004 | Paponneau |
| 6,830,589 B2 | 12/2004 | Erickson |
| 6,866,682 B1 | 3/2005 | An |
| 6,899,734 B2 | 5/2005 | Castro |
| 6,902,579 B2 | 6/2005 | Harms |
| 6,908,485 B2 | 6/2005 | Crozet |
| 6,908,495 B2 | 6/2005 | Northrop |
| 6,926,728 B2 | 8/2005 | Zucherman |
| 6,929,662 B1 | 8/2005 | Messerli |
| 6,991,653 B2 | 1/2006 | White |
| 7,008,432 B2 | 3/2006 | Schläpfer |
| 7,008,433 B2 | 3/2006 | Voellmicke |
| 7,014,659 B2 | 3/2006 | Boyer, II |
| 7,056,343 B2 | 6/2006 | Schäfer |
| 7,060,073 B2 | 6/2006 | Frey |
| 7,081,118 B2 | 7/2006 | Weber |
| 7,118,580 B1 | 10/2006 | Beyersdorff |
| 7,252,673 B2 | 8/2007 | Lim |
| 7,294,134 B2 | 11/2007 | Weber |
| 7,320,689 B2 | 1/2008 | Keller |
| 7,387,635 B2 | 6/2008 | Keller |
| 7,544,208 B1 | 6/2009 | Mueller |
| 7,641,693 B2 | 1/2010 | Gutlin |
| 7,648,529 B2 | 1/2010 | An |
| 7,691,147 B2 | 4/2010 | Gutlin |
| 7,708,779 B2 | 5/2010 | Edie et al. |
| 7,749,231 B2 * | 7/2010 | Bonvallet et al. ............... 606/99 |
| 7,819,922 B2 | 10/2010 | Sweeney |
| 7,981,157 B2 | 7/2011 | Castleman et al. |
| 7,988,699 B2 | 8/2011 | Martz |
| 2001/0007073 A1 | 7/2001 | Zucherman |
| 2001/0012938 A1 | 8/2001 | Zucherman |
| 2001/0016743 A1 | 8/2001 | Zucherman |
| 2001/0016776 A1 | 8/2001 | Zuckerman |
| 2001/0021850 A1 | 9/2001 | Zucherman |
| 2001/0029377 A1 | 10/2001 | Aebi |
| 2001/0031965 A1 | 10/2001 | Zucherman |
| 2001/0031969 A1 | 10/2001 | Aebi |
| 2001/0039452 A1 | 11/2001 | Zucherman |
| 2001/0053602 A1 | 12/2001 | Lee |
| 2002/0082695 A1 | 6/2002 | Neumann |
| 2002/0107200 A1 | 8/2002 | Chang |
| 2002/0123754 A1 | 9/2002 | Holmes |
| 2002/0183746 A1 | 12/2002 | Zucherman |
| 2003/0032964 A1 | 2/2003 | Watkins |
| 2003/0065330 A1 | 4/2003 | Zucherman |
| 2003/0149438 A1 | 8/2003 | Nichols |
| 2003/0163199 A1 | 8/2003 | Boehm |
| 2003/0171813 A1 | 9/2003 | Kiester |
| 2003/0187453 A1 * | 10/2003 | Schlapfer et al. ............... 606/90 |
| 2003/0191531 A1 | 10/2003 | Berry |
| 2003/0199980 A1 | 10/2003 | Siedler |
| 2003/0208272 A1 | 11/2003 | Crozet |
| 2003/0220650 A1 | 11/2003 | Major |
| 2003/0225414 A1 | 12/2003 | Shimp |
| 2003/0225416 A1 | 12/2003 | Bonvallet |
| 2003/0229355 A1 | 12/2003 | Keller |
| 2004/0010261 A1 | 1/2004 | Hoag |
| 2004/0039397 A1 | 2/2004 | Weber |
| 2004/0049271 A1 | 3/2004 | Biedermann |
| 2004/0059261 A1 * | 3/2004 | Grinberg ..................... 600/587 |
| 2004/0098129 A1 | 5/2004 | Lin |
| 2004/0106927 A1 | 6/2004 | Ruffner |
| 2004/0172129 A1 | 9/2004 | Schafer |
| 2004/0181283 A1 | 9/2004 | Boyer |
| 2004/0186569 A1 | 9/2004 | Berry |
| 2004/0199168 A1 | 10/2004 | Bertagnoli |
| 2004/0220582 A1 | 11/2004 | Keller |
| 2005/0015094 A1 | 1/2005 | Keller |
| 2005/0015095 A1 | 1/2005 | Keller |
| 2005/0021042 A1 * | 1/2005 | Marnay et al. ................. 606/99 |
| 2005/0043804 A1 | 2/2005 | Gordon |
| 2005/0055031 A1 | 3/2005 | Lim |
| 2005/0080425 A1 | 4/2005 | Bhatnagar |
| 2005/0085910 A1 | 4/2005 | Sweeney |
| 2005/0090898 A1 | 4/2005 | Berry |
| 2005/0101960 A1 | 5/2005 | Fiere |
| 2005/0113921 A1 | 5/2005 | An |
| 2005/0119665 A1 | 6/2005 | Keller |
| 2005/0143749 A1 * | 6/2005 | Zalenski et al. ................ 606/99 |
| 2005/0177173 A1 | 8/2005 | Aebi |
| 2005/0182416 A1 | 8/2005 | Lim |
| 2005/0187634 A1 | 8/2005 | Berry |
| 2005/0209697 A1 | 9/2005 | Paponneau |
| 2005/0216084 A1 | 9/2005 | Fleischmann |
| 2005/0234550 A1 | 10/2005 | Metz Stavenhagen |
| 2006/0004377 A1 | 1/2006 | Keller |
| 2006/0025777 A1 | 2/2006 | Weber |
| 2006/0030856 A1 | 2/2006 | Drewry |
| 2006/0036258 A1 | 2/2006 | Zucherman |
| 2006/0058879 A1 | 3/2006 | Metz Stavenhagen |
| 2006/0074431 A1 * | 4/2006 | Sutton et al. ................... 606/90 |
| 2006/0129241 A1 | 6/2006 | Boyer |
| 2006/0200244 A1 | 9/2006 | Assaker |

| 2006/0217712 A1 | 9/2006 | Mueller |
| 2007/0028710 A1 | 2/2007 | Kraus |
| 2007/0123987 A1 | 5/2007 | Bernstein |
| 2007/0161999 A1 | 7/2007 | Biedermann |
| 2007/0168040 A1 | 7/2007 | Raymond |
| 2007/0255408 A1 | 11/2007 | Castleman et al. |
| 2008/0009864 A1 | 1/2008 | Forton |
| 2008/0027544 A1 | 1/2008 | Melkent |
| 2008/0039948 A1 | 2/2008 | Biedermann |
| 2008/0269901 A1 | 10/2008 | Baynham |
| 2009/0005874 A1 | 1/2009 | Fleischmann |
| 2009/0036985 A1 | 2/2009 | Whiting |
| 2009/0276050 A1 | 11/2009 | Biedermann |

FOREIGN PATENT DOCUMENTS

| EP | 1090703 | 4/2001 |
| EP | 1188424 | 3/2002 |
| EP | 1491165 | 12/2004 |
| WO | 9963913 | 12/1999 |
| WO | WO 02071986 | 9/2002 |

OTHER PUBLICATIONS

Coumans, "Use Of The Telescopic Plate Spacer In Treatment Of Cervical And Cervicothoracic Spine Tumors", *Neurosurgery*, Aug. 2005 vol. 51(2), pp. 417-426.

Pederson, "Thermal Assembly Of A Biomimetic Mineral/Collagen Composite", Biomaterials. Nov. 2003; vol. 24(26), pp. 4881-4890.

Pflugmacher, "Biomechanical Comparison Of Expandable Cages For Vertebral Body Replacement In The Thoracolumbar Spine", *SPINE*, Jul. 1, 2004, vol. 29(13), pp. 1413-1419.

Woiciechowsky, "Distractable Vertebral Cages For Reconstruction After Cervical Corpectomy", *SPINE*, Aug. 1, 2005, vol. 30(15), pp. 1736-1741.

Kandziora, "Biomechanical Comparison Of Expandable Cages for Vertebral Body Replacement In The Cervical Spine", *J Neurosurg*, Jul. 2003, vol. 99(1), pp. 91-97.

Thongtrangan, "Vertebral Body Replacement With An Expandable Cage For Reconstruction After Spinal Tumor Resection", *Neurosurg Focus*, Nov 15, 2003, vol. 15(5) p. E8.

Krbec, "Replacement of the Vertebral Body With an Expansion Implant", Acta Chir Orthop Traumataol Cech , 2002, pp. 158-162, vol. 69(3)—Abstract Only.

Kazan, "Percutaneous Anterior Odontoid Screw Fixation Technique. A New Instrument And A Cadaveric Study", Acta Neurochir Wien, 1999, pp. 521-524, vol. 141(5)—Abstract Only.

Khodadadyan-Klostermann, "Expandable Cages: Biomechanical Comparison Of Different Cages For Ventral Spondylodesis In The Thoracolumbar Spine", Chirug, Jul. 2004, pp. 694-701, vol. 75(7)—Abstract Only.

* cited by examiner

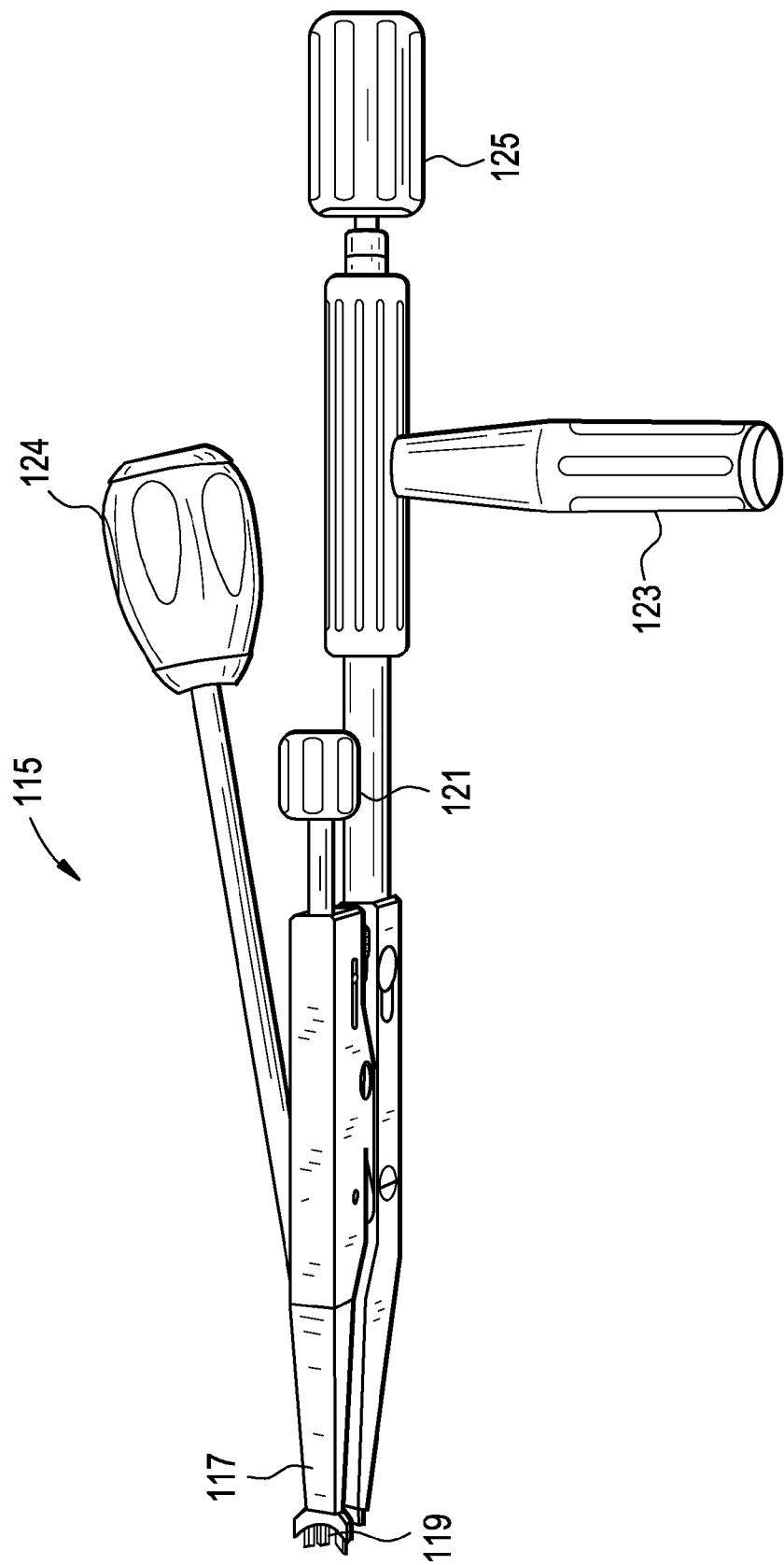

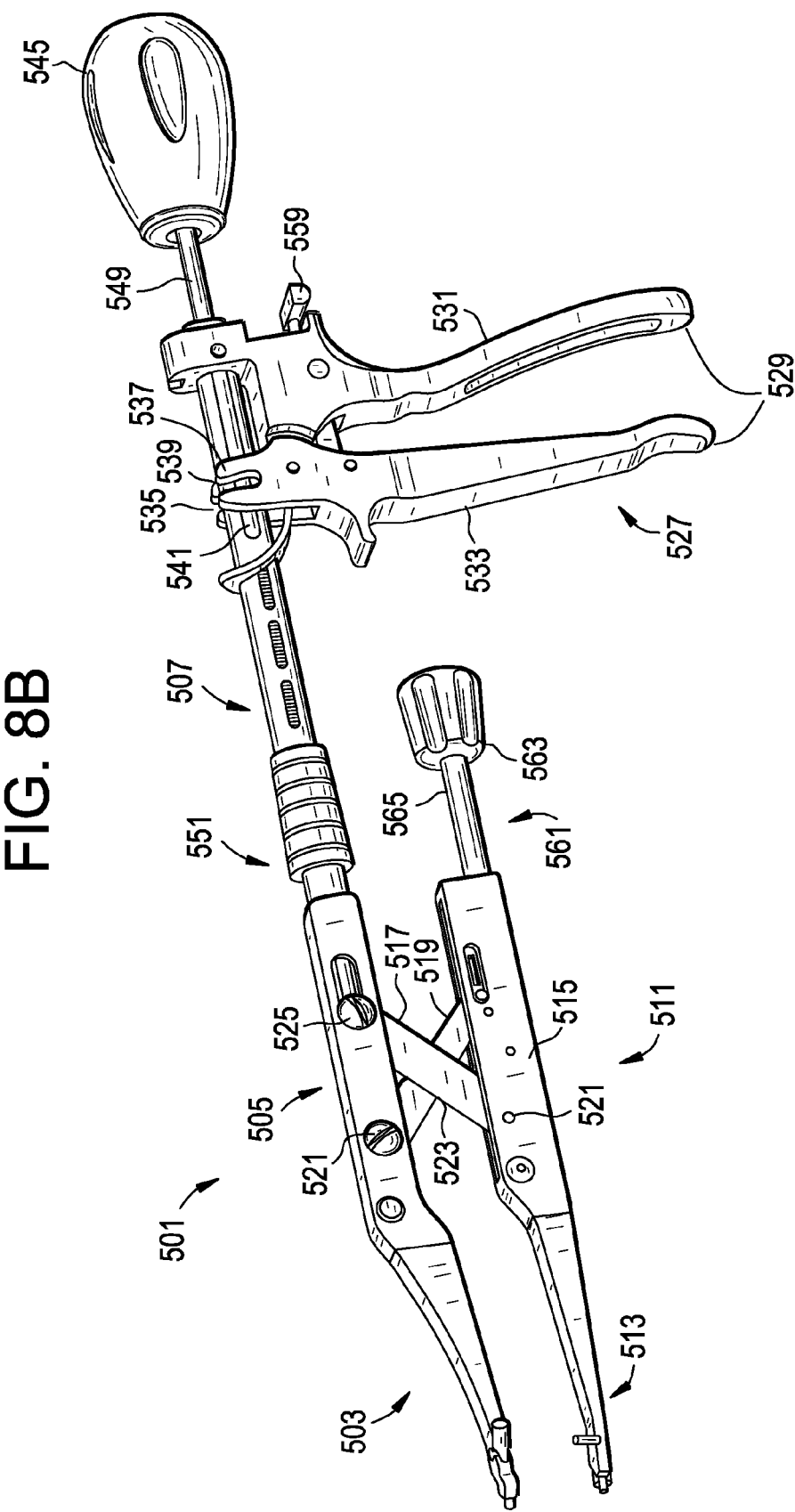

180 Deg  90 Deg  0 Deg

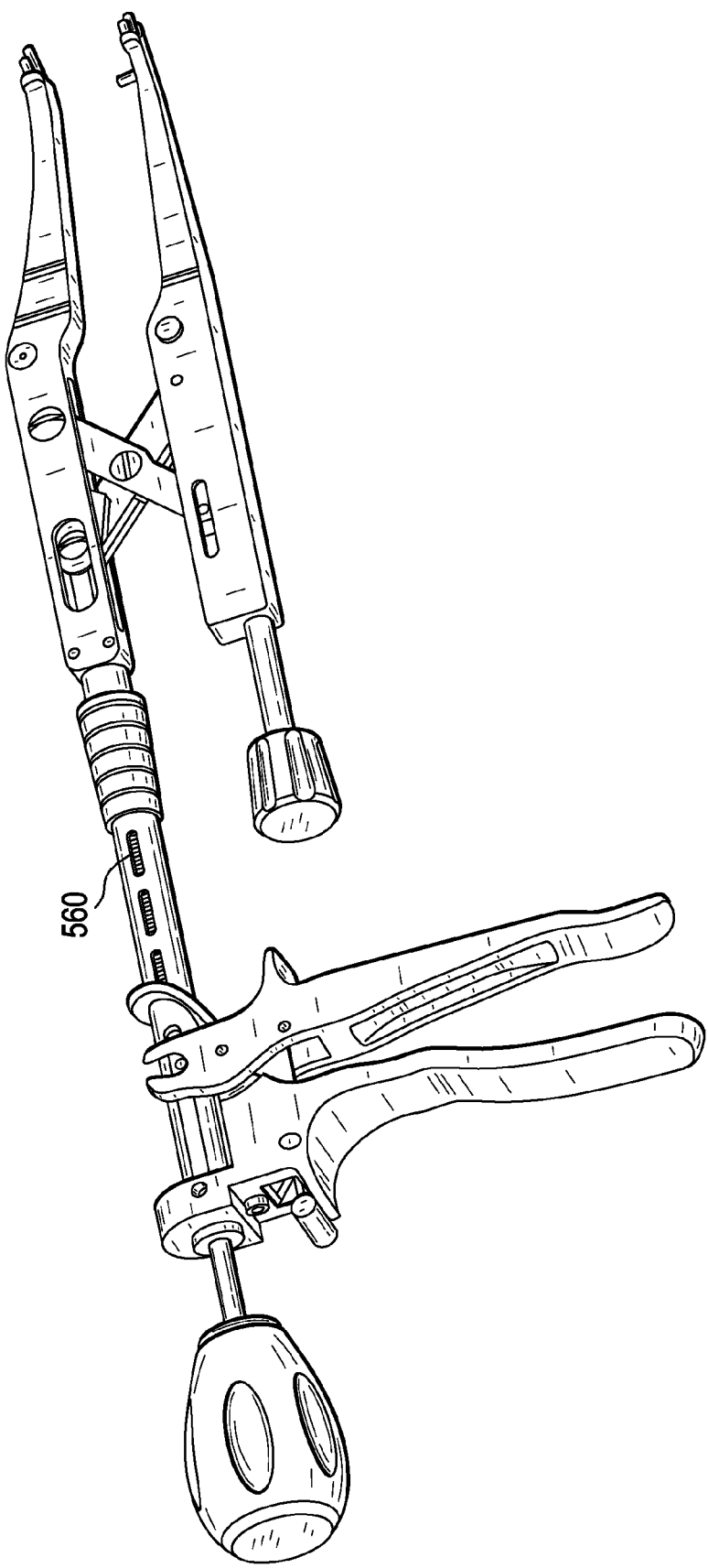

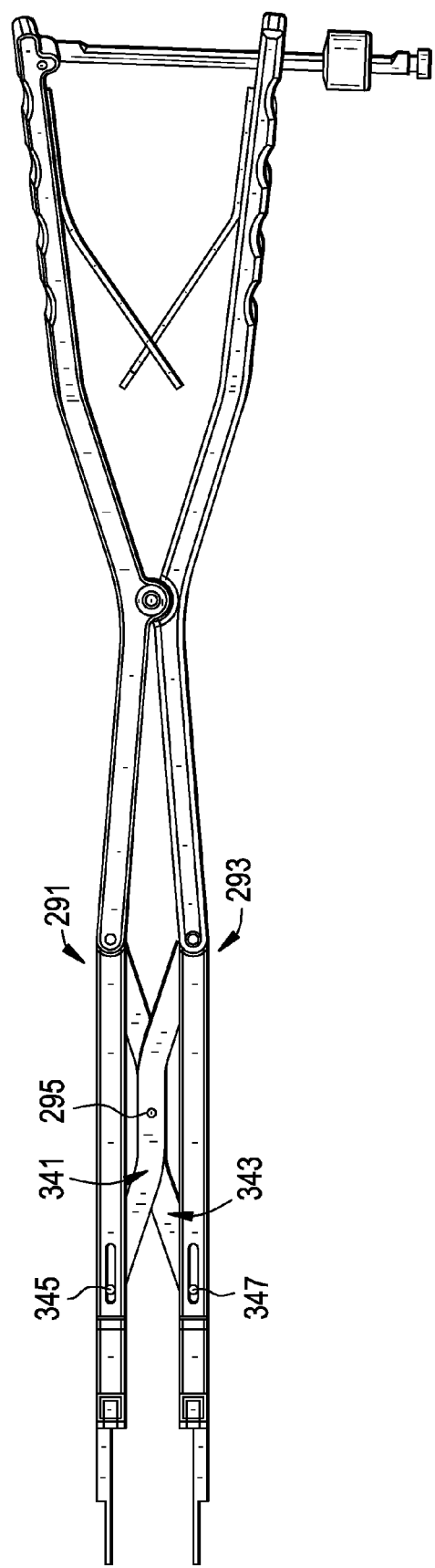

INSTRUMENTS FOR EXPANDABLE CORPECTOMY SPINAL FUSION CAGE

CONTINUING DATA

This continuation-in-part patent application claims priority from co-pending U.S. Ser. No. 11/960,623, filed Dec. 19, 2007, entitled "Expandable Corpectomy Spinal Fusion Cage" (Sommerich) (DEP6073USNP)

BACKGROUND OF THE INVENTION

One conventional spinal implant used in corpectomy cases is an intervertebral spacer for insertion between two vertebrae, wherein the spacer has an adjustable axial height, an annular first member and a second member which is guided within the first member and displaceable in axial direction relative to the first member for adjustment of the overall height.

Conventional spacers of this type of are often expanded by a threaded connection between the outer surface of the inner member and the inner surface of the outer member. The opposite ends of the spacer are often provided with spikes for secure seating into the adjacent vertebra. However, the requirement of rotating the members around the longitudinal axis also rotates the spikes, thereby risking injury to the adjacent vertebrae.

U.S. Pat. No. 6,200,348 (Biedermann) discloses a spacer that is expandable without the need for rotation. The locking mechanism of the U.S. Pat. No. 6,200,348 includes a i) a pair of set screws, each set screw having a hemispherical distal end that seats in an outer annulus, and ii) a row of mating hemispherical recesses extending into an inner annulus.

SUMMARY OF THE INVENTION

The present inventors have appreciated that although the spacer design disclosed in U.S. Pat. No. 6,200,348 has advantageously eliminated the need to rotate the pair of sleeved cage components in order to expand its height, it nonetheless does not contain a graft window. A graft window is a large opening in the face of the cage—an opening much larger than the diamond shaped holes provided in U.S. Pat. No. 6,200,348—used to insert graft into the cage. Providing a graft window is helpful in that it provides the surgeon with an access port into the center space of the cage through which the surgeon may insert bone graft into the cage. When a graft window is not provided, bone graft must be inserted into the cage prior to insertion of the cage into the spine (i.e., when the cage is in its unexpanded configuration). Thus, when the cage is later inserted into the spine and then expanded, the newly expanded portion of the cage contains no graft. Providing a graft window is helpful in that it allows the surgeon to place the cage into the spine, expand the cage and then fill the expanded cage with bone graft. Accordingly, there is no unfilled space in the expanded inserted cage having a graft window.

Therefore, in accordance with the present invention, there is provided a spacer for insertion between two vertebrae, the spacer having a variable axial height and comprising a first member and a second member guided within the first member to be slidable relative thereto in an axial direction thereof for adjusting an overall height,
wherein the second member comprises an outer wall and ratchet notches provided at its outer wall facing the first member and extending in the axial direction,
wherein the first member comprises a wall having an engagement member, which cooperates with the ratchet notches for adjusting the overall height of the spacer, and
wherein the first member has a graft window therein for inserting graft material therethrough.

However, when the present inventors set out to modify the cage of U.S. Pat. No. 6,200,348 with a graft window, they found that inclusion of the graft window would either require removal of the locking mechanism to another location (such as the distal portion of the inner annulus, as shown in FIG. 6 below) or require that the graft window be very small.

The present inventors thus set out to redesign the locking mechanism of U.S. Pat. No. 6,200,348 so that inclusion of a graft window would not require removal of the locking mechanism to another location, nor require that the graft window be very small.

The present inventors found that replacing the set screw/spherical recess locking mechanism of U.S. Pat. No. 6,200,348 with a new mechanism solved the above noted problem. The new mechanism is an engagement member which comprises i) a set screw and ii) a pressure plate having an outer face contacting the set screw and an inner face having teeth adapted to mate with the ratchet notches of the second member Moreover, the present inventors found that the new locking mechanism imparted a superior strength to the cage so that only one set screw was needed to lock the cage in its expanded condition.

Also in accordance with the present invention, there is provided a spacer for insertion between two vertebrae, said spacer having a variable axial height and comprising a first member and a second member guided within the first member to be slidable relative thereto in an axial direction thereof for adjusting an overall height,
wherein the second member comprises an outer wall and ratchet notches provided at its outer wall facing the first member and extending in the axial direction,
wherein the first member comprises a wall having an engagement member, which cooperates with the ratchet notches for adjusting the overall height of the spacer, and
wherein the engagement member comprises i) a set screw and ii) a pressure plate having an outer face contacting the set screw and an inner face having teeth adapted to mate with the ratchet notches of the second member.

DESCRIPTION OF THE FIGURES

FIG. 7 discloses an inserter-expander instrument for inserting and expanding the cage of the present invention.

FIG. 8b discloses a second view of the inserter/expander instrument provided with a pistol grip FIGS. 9a-9c disclose the pistol grip portion of the instrument rotated to three positions.

FIGS. 10a-10f disclose an embodiment of the second distractor and various portions thereof.

DETAILED DESCRIPTION OF THE INVENTION

For the purposes of the present invention "spacer" and "cage" are used interchangeably.

Figure 1A:
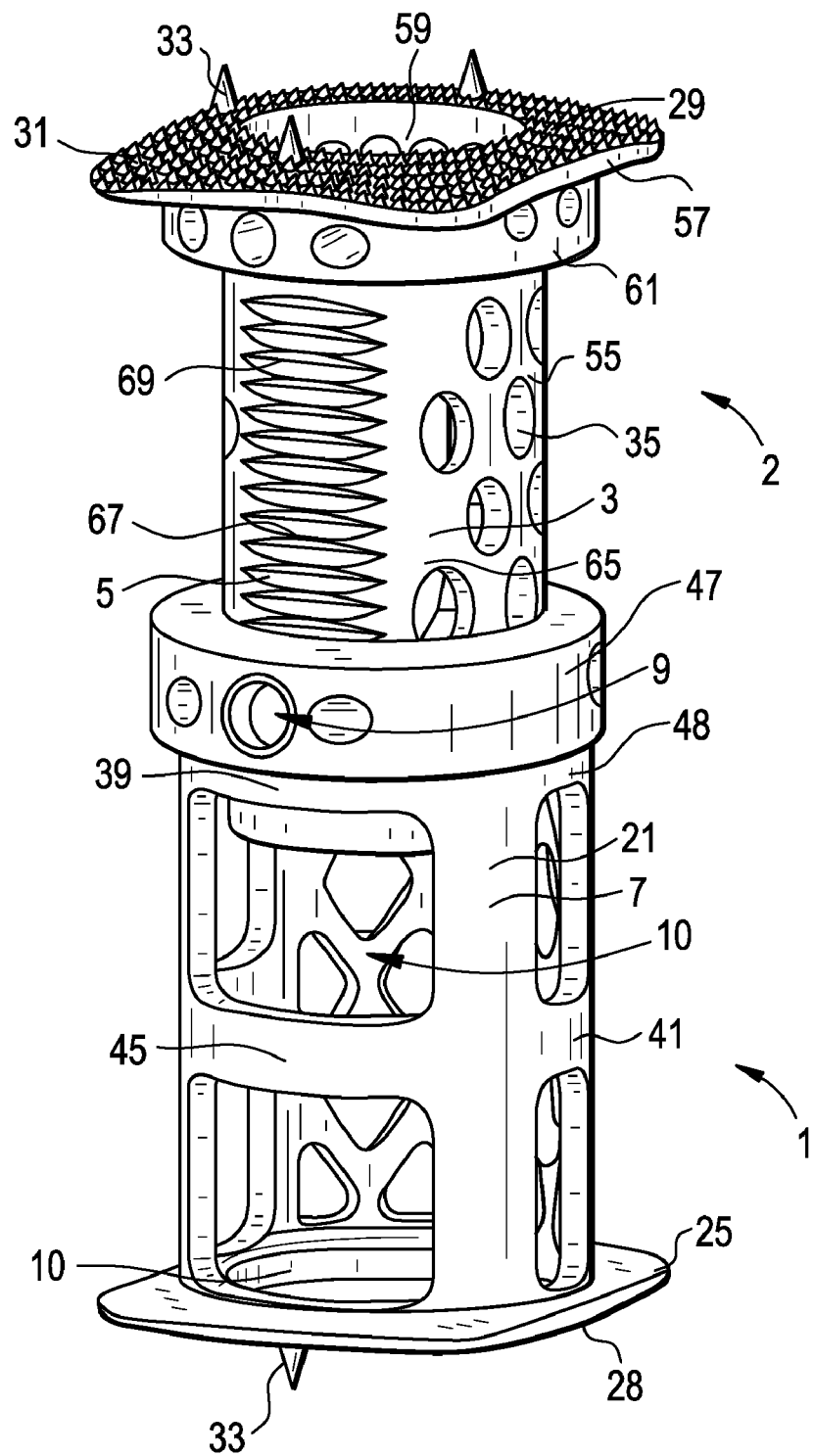
FIGS. 1a and 1b disclose front and back views of a cage of the present invention.

Now referring to FIG. 1 there is provided a spacer for insertion between two vertebrae, the spacer having a variable axial height and comprising a sleeve-shaped first member 1 and a second member 2 guided within the first member to be slidable relative thereto in an axial direction thereof for adjusting an overall height, wherein the second member comprises an outer wall 3 and ratchet notches 5 provided at its outer wall facing the first member and extending in the axial direction, and wherein the first member comprises a wall 7 having an engagement member 9, which cooperates with the ratchet notches for adjusting the overall height of the spacer, wherein the first member has a window 10 therein for inserting graft material therethrough, and wherein the engagement member 9 comprises i) a set screw 11 and ii) a pressure plate 13 having an outer face 15 contacting the set screw and an inner face 17 having teeth 19 adapted to mate with the ratchet notches of the second member.

The first member generally has a tubular shape comprising a first annulus 21. The outer end of the first member should be adapted to seat upon a lower vertebral endplate, and so a substantially flat endplate 25 is generally attached to the outer end 27 of the first annulus. This endplate generally has a hole in its center and extends outwardly substantially radially from the outer end of the annulus. The outer face 28 of the endplate should be adapted to grip the lower vertebral endplate and so is generally provided with roughened features 29. These roughened features may be a plurality of uniformly distributed, pointed teeth 31 that bite into the adjacent endplate. In other embodiments, the teeth may be non-uniformly distributed. For further insuring that the endplate will be stably seated into the vertebral endplate, the outer face of the endplate may also have a few long spikes 33 extending therefrom. In some embodiments, the endplate has an overall convex shape in order to suitably conform to the overall concave shape of the natural vertebral endplate in which it seats. In some embodiments (as in FIG. 1c), the endplate has a wedge cross-section in order to conform to the lordosis adopted by the natural spine in the region of the implant. Typically, the wedge is designed to provided a lordotic angle of between about 0 and about 24 degrees, more typically between about 6 and about 12 degrees. The wedge may also be designed to provided a kyphotic angle of between about 0 and about −12 degrees, In general, the outer dimensions of the endplates of the present invention are between about 16 mm and about 30 mm (e.g., 16×20; 20×23 and 24×30).

The annular portion of the first member also comprises a plurality of uniformly distributed, transverse, through-holes 35. These throughholes are generally about 2-8 mm in diameter, and provide a means for bone growth therethrough. The holes are preferably of diamond shape, although other shapes such as triangles may be used. When in a diamond shape, suitable sizes include 2.5 mm×3.5 mm shapes to 5 mm×7 mm shapes. In the particular FIGS. 1a and 1b, the throughholes have a diamond shape. The diamond shape allows the annulus material to make a mesh pattern in the wall that has structural advantages. However, any conventional shape may be used for the through-hole pattern. In some embodiments, the plurality of throughholes occupy only the distal portion 37 of the annulus. In such an embodiment, graft windows may be placed both on the proximal 39 and lateral 41 portions of the annulus. This has the advantage of allowing the surgeon to place bone graft into the cage from a variety of angles. In some embodiments, the plurality of throughholes occupy not only the distal portion of the first annulus, but also the lateral portions as well. In such an embodiment, graft windows may be placed only through the proximal portion of the annulus, but the cage has the structural advantage of extra strength.

The first member generally has at least one graft window 10 therein. The graft window functions both as a path through which the surgeon can place bone graft into the cage, but also as a means for bone growth therethrough. In other embodiments, the first member has a plurality of graft windows therein. When a face of the annulus has been selected for graft windows, in preferred embodiments, two graft windows 43 are placed one on top of the other, being separated by a bar 45. This bar enhances the strength of the cage. In the particular cage shown in FIG. 1a, there are two graft windows on the proximal face of the annulus, two graft windows on the left lateral face of the annulus and two graft windows on the right lateral face of the annulus. This configuration represents a balance between providing surgeon flexibility (through the inclusion of multiple faces with graft windows) and cage strength (through the use of a lateral bar between windows on any face). Each window typically has a diameter of between about 5 mm and about 20 mm. Typical windows measure 5.5 mm×5.6 mm to 12 mm×15.75 mm to 17.5 mm×12 mm.

The first member may preferably include a reinforcing collar 47 surrounding the inner (upper) end portion 48 of the first annulus. The function of the reinforcing collar is to strengthen the first member and reduce deflection when the screw is tightened. The reinforcing collar also generally has a threaded screw hole extending radially therethrough. This threaded screw hole is adapted for threadable passage of a threaded locking set screw therethrough.

Figure 2A:
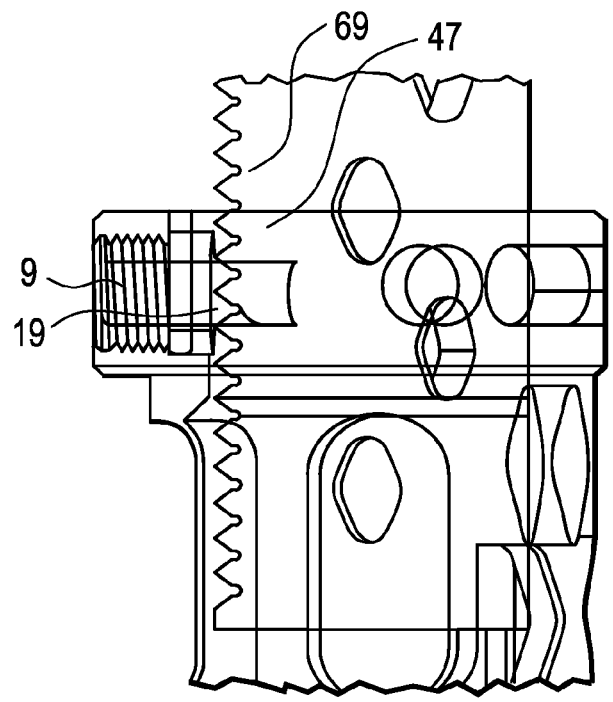
FIG. 2a discloses a cage of the present invention in which the teeth of the pressure plate mate with the notches on the inner annulus.

Now referring to FIG. 2a, the first member comprises a collar 47 having an engagement member 9 therein, and the engagement member cooperates with the ratchet notches of the second member for adjusting a desired overall height of the spacer.

Figure 2B:
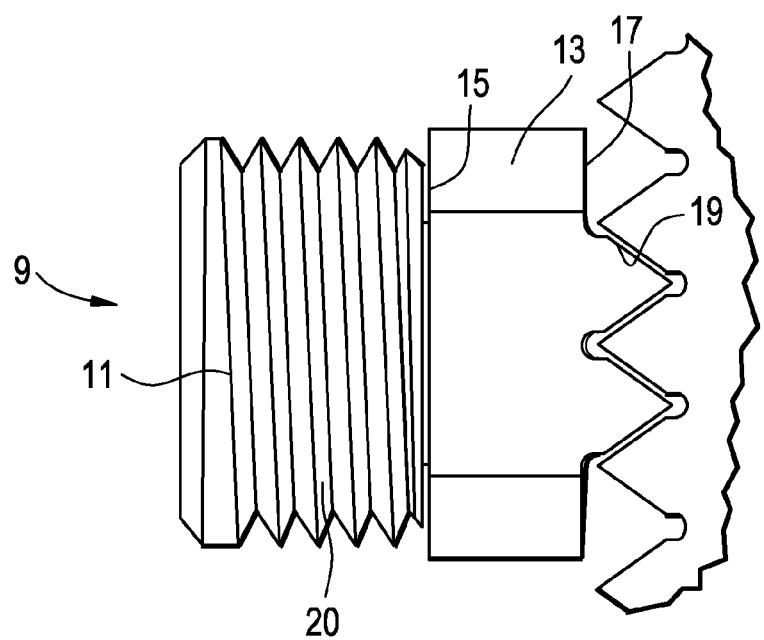
FIG. 2b discloses details of the engagement mechanism of the present invention.

Now referring to FIG. 2b, there is provided a more detailed understanding of the engagement member. The engagement member 9 comprises i) a set screw 11 and ii) a pressure plate 13 having an outer face 15 contacting the set screw and an inner face 17 having teeth 19 adapted to mate with the ratchet notches of the second member.

In some embodiments, as in FIG. 2b, a cylindrical outer surface 20 of the set screw is threaded to allow its advance toward the second member. In some embodiments, as in FIGS. 3a and 3b, the set screw is tubular with internal axial recesses 22 therein extending along its axis. These axial recesses mate with a screwdriver, thus allowing the screw to be rotated and thereby advanced towards the second member.

The set screw further has a neck and head extension 49 extending from its distal end 50, wherein the extension is shaped so as to both provide engagement with a corresponding recess 51 of the pressure plate and allow its rotation during that engagement.

Figure 3A:
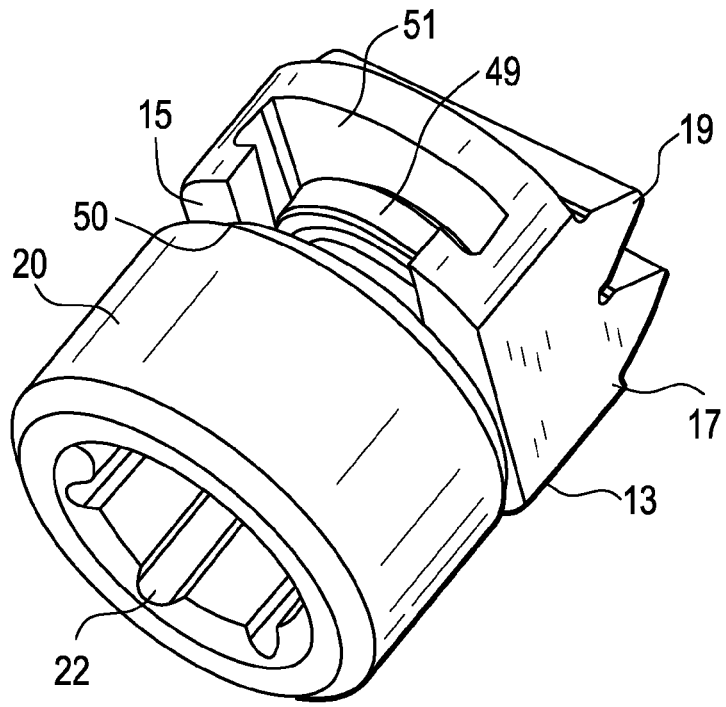
FIG. 3a discloses a perspective view of the engagement member of the present invention.
Figure 3B:
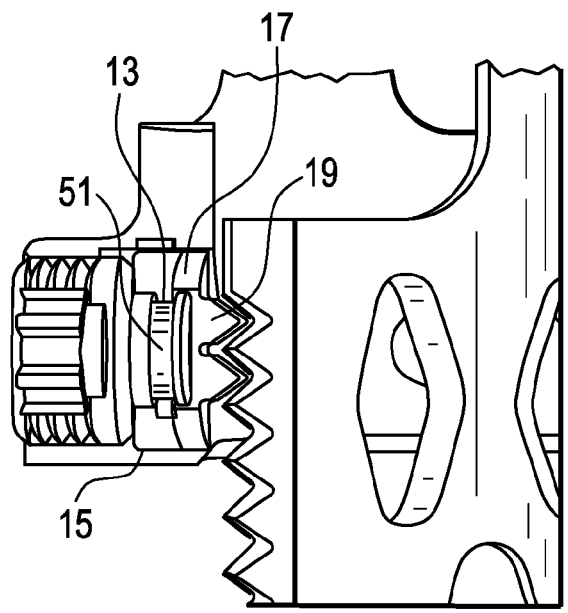
FIG. 3b discloses a cross-section of the engagement mechanism of the present invention having a pressure plate.

Now referring to FIGS. 3a and 3b, the pressure plate 13 has an outer face 15 contacting the set screw and an inner face 17 having teeth 19 adapted to mate with the ratchet notches of the second member. The outer face has a neck and head recess 51 therein that corresponds with the head and neck extension of the set screw so as to both provide engagement with a corresponding extension of the set screw and allow rotation of the set screw during that engagement. The pressure plate is seated on the inside face of the collar.

The inner face of the pressure plate has at least two elongated teeth 19 thereon forming at least one notch therebetween. The tips of the teeth are preferably spaced apart a distance of between about 1 mm and 2 mm, generally about 1.5 mm. The spacing can be larger or smaller than these values, with smaller being preferable.

Figure 1B:
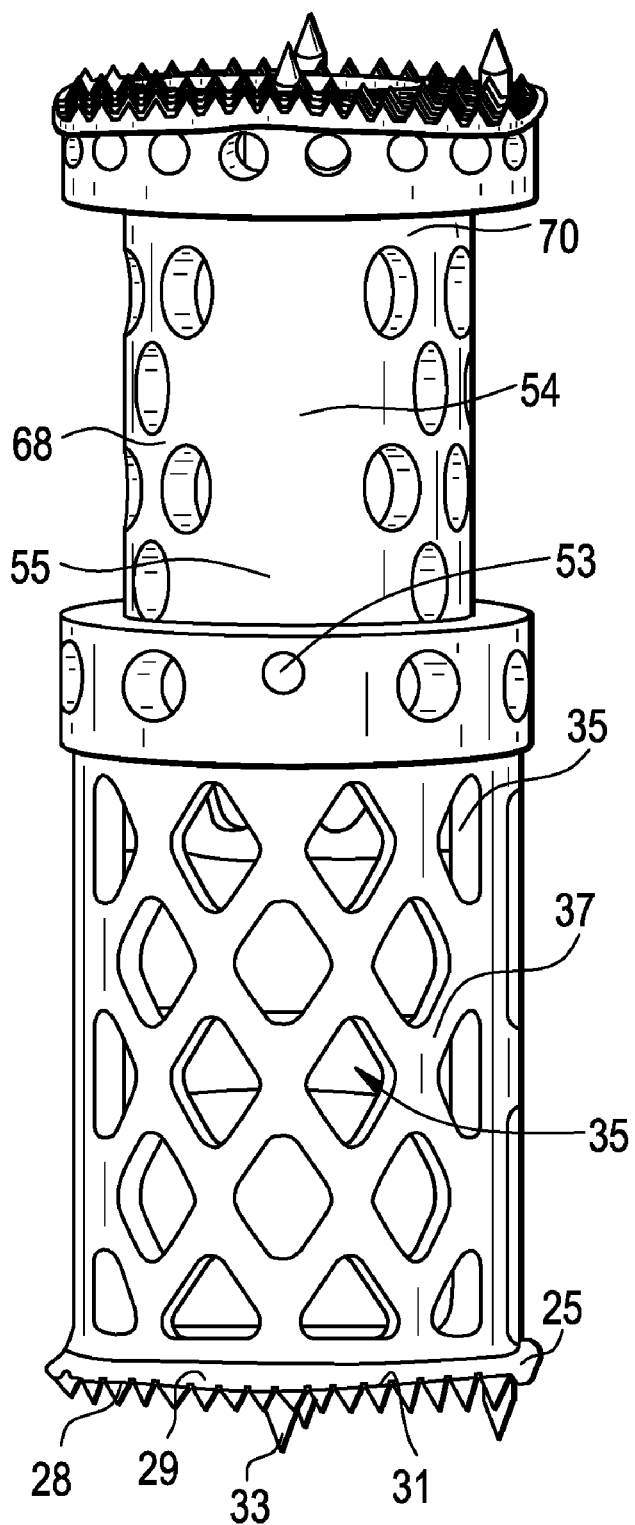
Figure 1C:
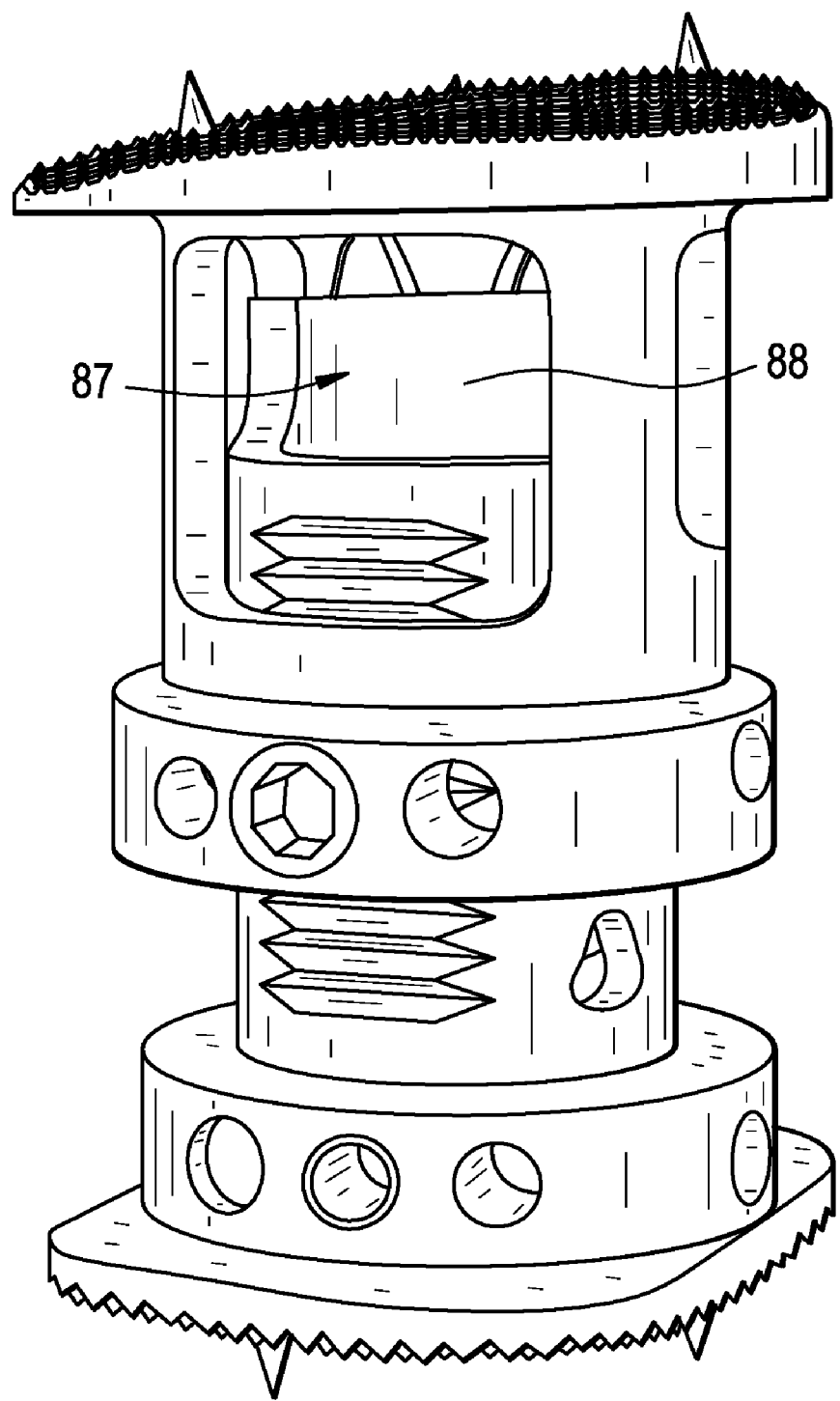
FIG. 1c discloses a cage of the present invention having windows in both annuluses.

Now referring to FIG. 1b, the distal 37 portion of the first member also has an assembly pin 53 extending radially inward from the collar. This assembly pin slidably mates with a corresponding assembly groove 54 of the second member in order to maintain the second member in a slidable orientation within the first member, and to retain the first member to the second member.

Still referring to FIG. 1b, the second member generally has a tubular shape comprising a second annulus 55. The outer diameter of the second annulus should be slightly smaller than the inner diameter of the first annulus of the first member, in order to provide slidable reception of the second annulus within the first member.

The outer end of the second member should be adapted to seat upon an upper vertebral endplate, and so a substantially flat endplate 57 is generally attached to the outer end 59 of the second annulus 55. This endplate generally has a hole in its center and extends outward substantially radially from the upper end of the annulus. The outer face of the endplate should be adapted to grip the upper vertebral endplate and so is generally provided with roughened features 29. These roughened features may be a plurality of uniformly (or non-uniformly) distributed, pointed teeth 31 that bite into the adjacent endplate. For further insuring that the endplate will be stably seated into the vertebral endplate, the outer face of the endplate may also have a few long spikes 33 extending therefrom. In some embodiments, the endplate has an overall convex shape in order to suitably conform to the overall concave shape of the natural vertebral endplate in which it seats.

The annular portion of the second member also comprises a plurality of uniformly distributed, transverse, through-holes 35. These throughholes are generally of the throughhole size discussed above, and provide a means for bone growth therethrough. In this particular FIG. 1a, the throughholes have a diamond shape. The diamond shape allows the second annulus material to make a mesh pattern that has structural advantages. However, any conventional shape may be used for the through-hole pattern. In some embodiments, the plurality of throughholes occupy each of the lateral faces of the posterior portion of the second annulus.

The second member may preferably include a reinforcing collar 61 surrounding the outer (upper) end portion 59 of the second annulus. The function of this reinforcing collar is to allow for instrument attachment. The reinforcing collar also generally has a plurality of through-holes 63 extending radially therethrough. These throughholes function as areas for instrument attachment, and as areas for bone growth and vascularization.

The proximal portion 65 of the second annulus has a plurality of elongated teeth 67 thereon forming at least one notch 69 therebetween. These teeth and notches form a row extending up the outside of the annulus. Typically, the annulus of the second member has at least ten elongated notches thereon. These notches are formed to compliment the teeth of the pressure plate. The apices of the notches on the second member are generally spaced apart a distance of between about 1 mm and 2 mm, generally about 1.5 mm. The spacing can be larger or smaller than these values, with smaller being preferable.

The distal 70 portion of the second annulus of the second member also has an assembly groove 54 extending inwardly and axially along the outside 68 of the second annulus. This assembly groove mates with the corresponding assembly pin of the first member in order to maintain the second member in a slidable orientation within the first member.

Once the overall height of the cage has been determined by the surgeon and the relative disposition of the first and second members set accordingly, the set screw is then rotated by the surgeon using a screwdriver. The set screw acts to advance the pressure plate so that the teeth on the pressure plate contact the ratchet notches of the second member, thereby locking the desired overall height of the cage.

The general design of the cage of the present invention provided in FIGS. 1a and 1b may be altered in order to be suit the approach used to implant the cage.

Figure 4A:
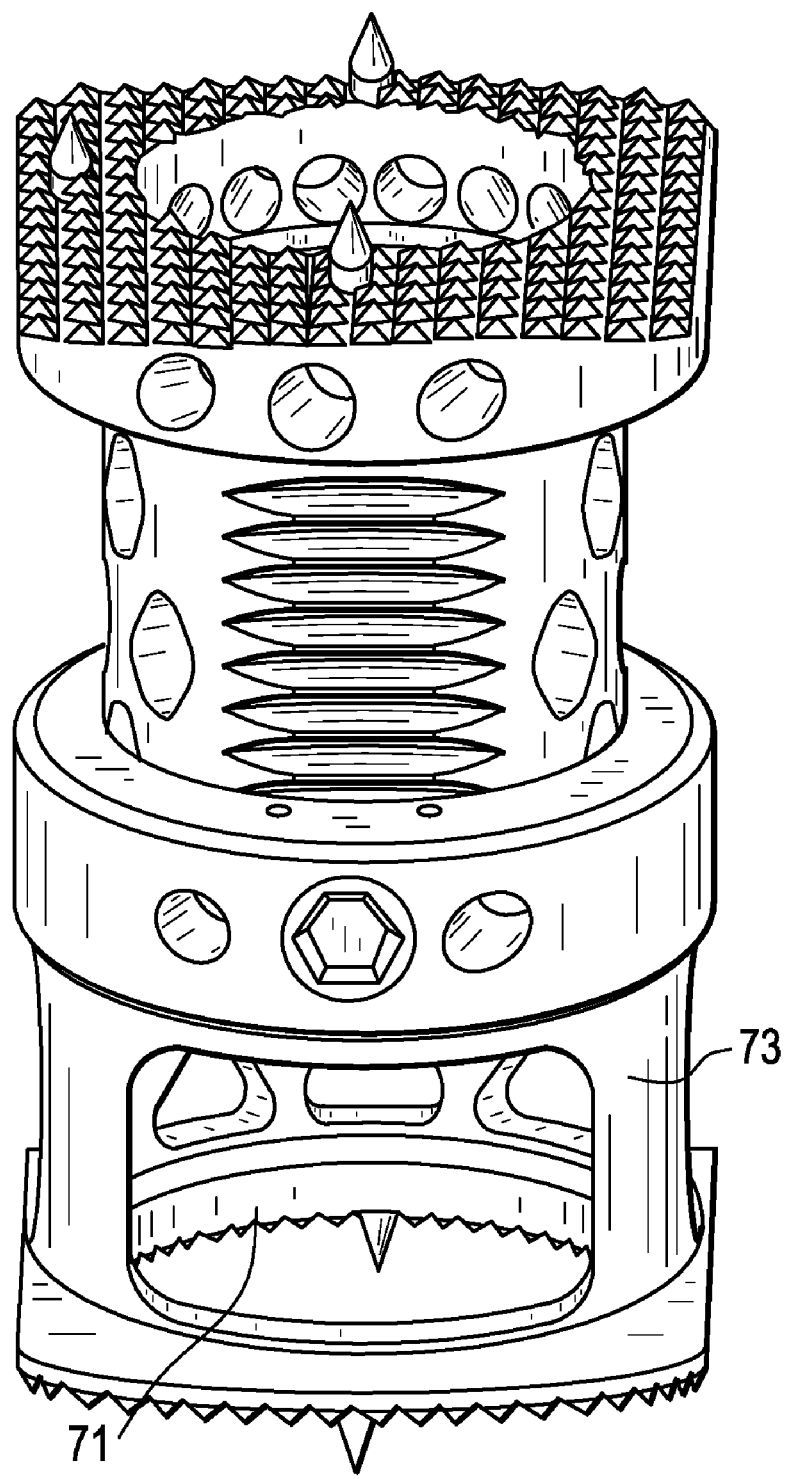
FIGS. 4a-4c disclose cages of the present invention respectively adapted for lateral, direct anterior and postero-lateral insertion.

For example, now referring to FIG. 4a, there is provided a cage suited for a lateral approach. A lateral approach is generally characterized by a surgical opening on a lateral side of the spine. Accordingly, the Lateral cage of FIG. 4a possesses a graft window 71 that opens onto a lateral side 73 of the outer annulus. This allows the surgeon to conveniently place graft into the cage through the lateral surgical opening used to approach the spine.

Figure 4B:
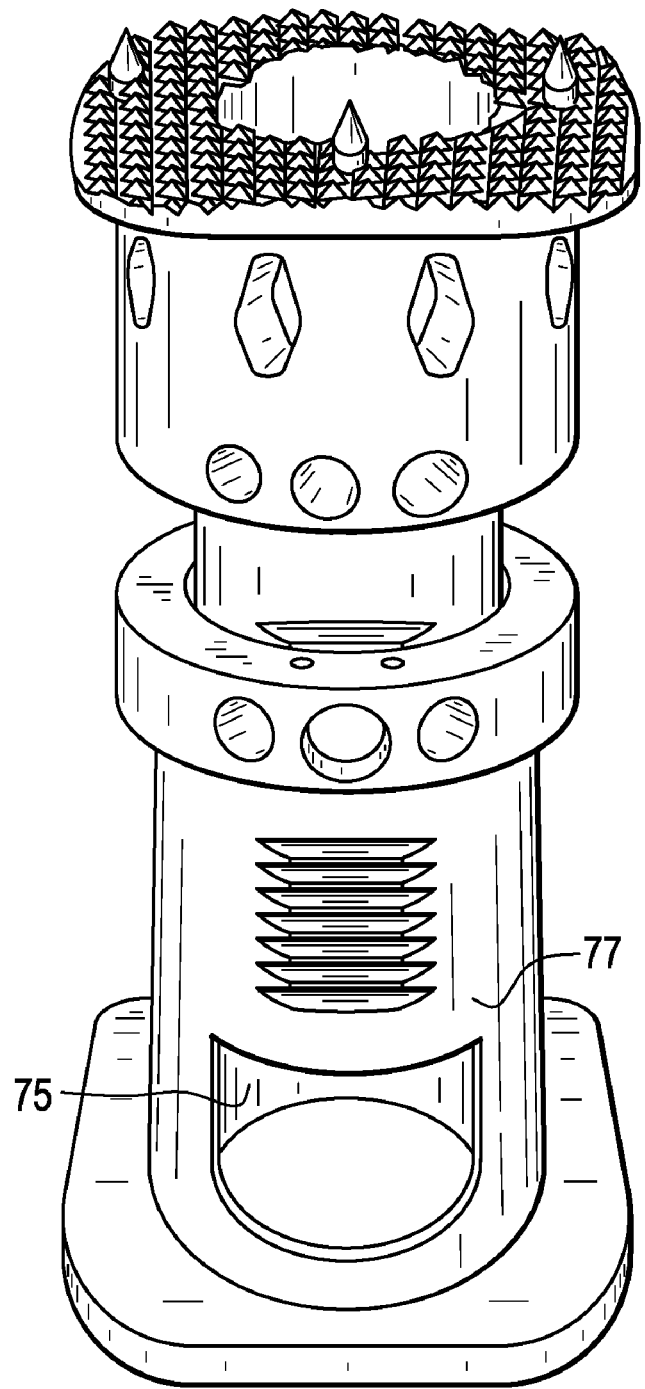

For example, now referring to FIG. 4b, there is provided a cage suited for a direct anterior approach. A direct anterior approach is generally characterized by surgical opening on the anterior portion of the spine. Accordingly, the Direct Anterior cage of FIG. 4b possesses a graft window 75 that opens onto a generally anterior side 77 of the outer annulus. In some embodiments, the window is oriented 45 degrees to the endplates in order to avoid the great vessels. This allows the surgeon to conveniently place graft into the cage through the anterior surgical opening used to approach the spine.

Figure 4C:
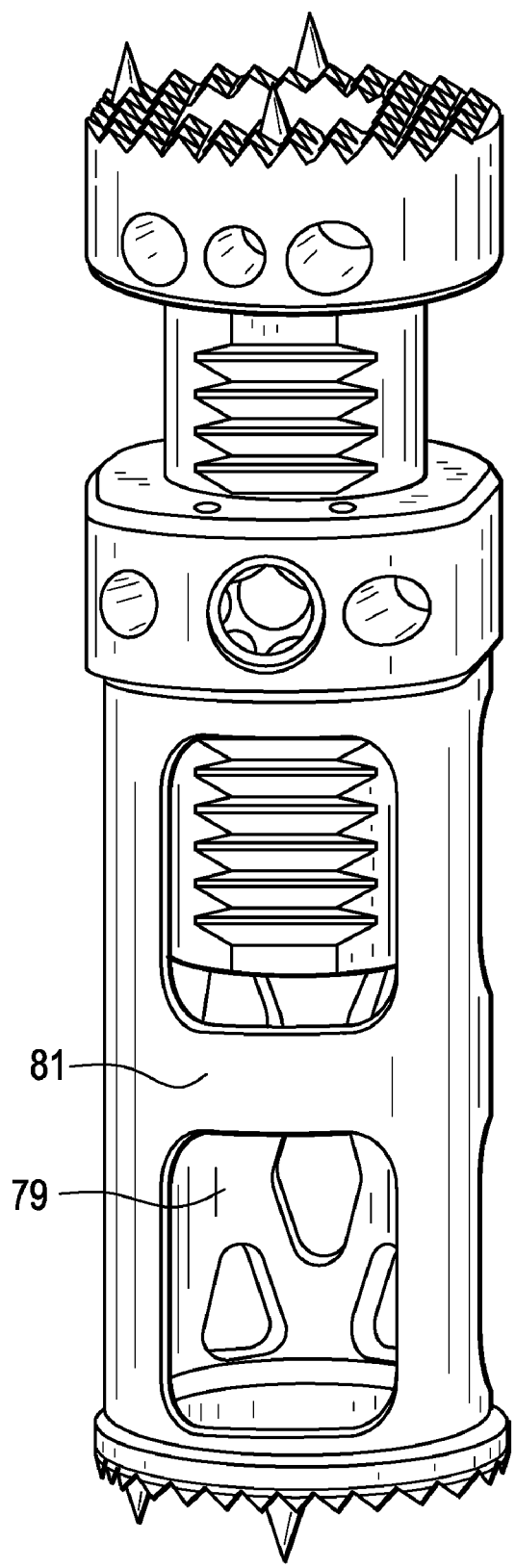

For example, now referring to FIG. 4c, there is provided a cage suited for a postero-lateral approach. A postero-lateral approach is generally characterized by a surgical opening on a postero-lateral side of the spine. Accordingly, the postero-lateral cage of FIG. 4c possesses a graft window 79 that opens onto a postero-lateral side 81 of the outer annulus. This allows the surgeon to conveniently place graft into the cage through the postero-lateral surgical opening used to approach the spine. The window of this cage is placed so that it opens to the surgeon. In some embodiments, the endplates of this cage are substantially circular so as not to be approach-specific.

Typically, the cages of the present invention are designed to occupy either one, two or three levels of a thoracolumbar corpectomy. In some embodiments having either 16 mm or 20 mm endplate dimensions, the height of the cage can be between 22 mm and 72 mm. In some embodiments having 24 mm endplate dimensions, the height of the cage can be between 22 mm and 110 mm. In general, the cage is designed to expand its height in an increment of between about 8.5 mm to about 25 mm. Cages can be designed to overlap in height ranges with their adjacent sizes. For example a first cage can range in height from 25 to 33.5 mm, while a second cage can range in height from 28.5 mm to 38.5 mm in height.

Figure 5:
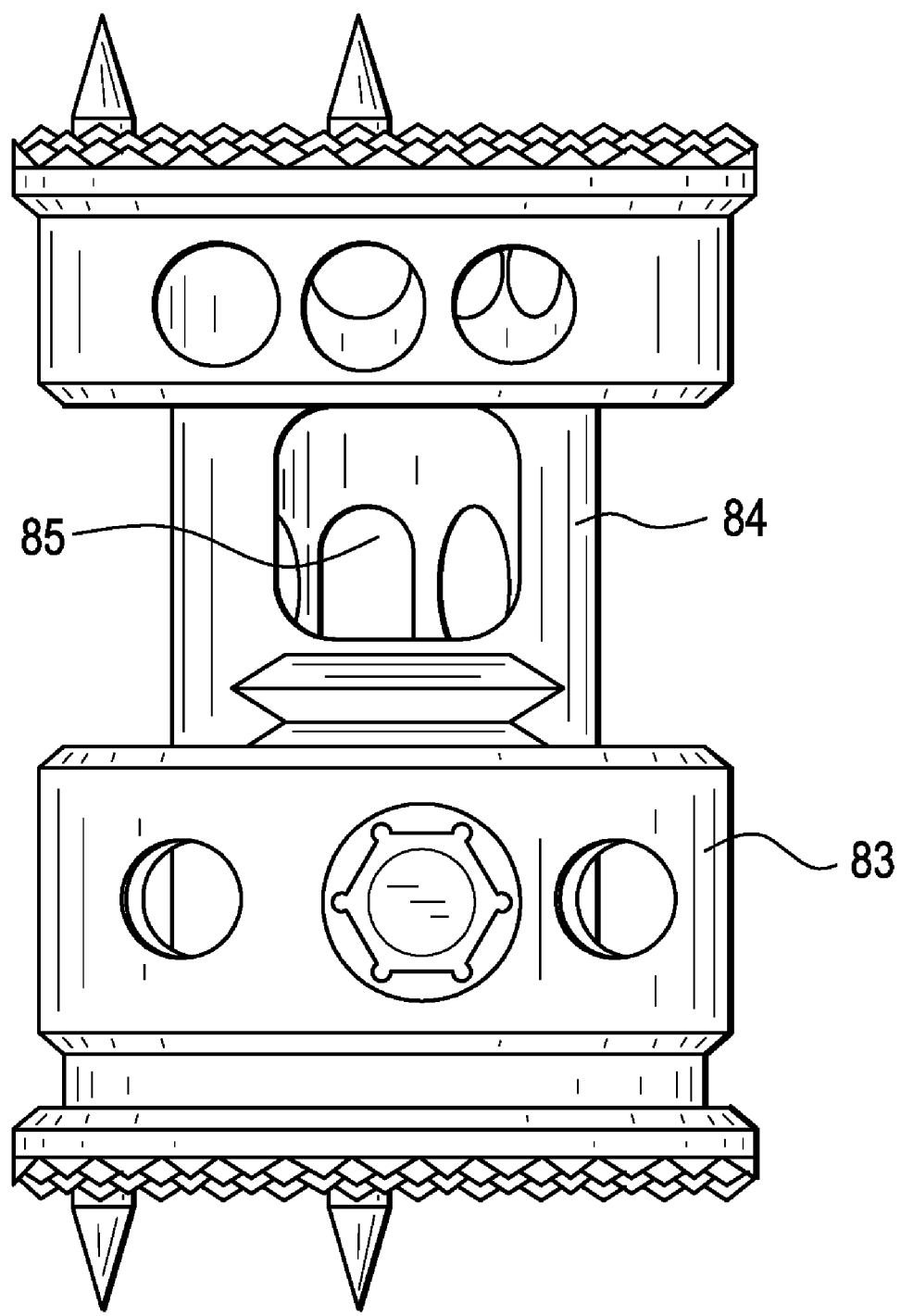
FIG. 5 discloses a cage having the graft window on its inner annulus.

When the cage of the present invention is generally short (i.e., an overall height of less than about 40 mm), it is advantageous to provide the sole graft window on the second (inner) annulus. Now referring to FIG. 5, there is provided a spacer for insertion between two vertebrae, the spacer having a variable axial height and comprising a sleeve-shaped first outer member 83 and a second inner member 84 guided within the first member to be slidable relative thereto in an axial direction thereof for adjusting an overall height, wherein the second member comprises an outer wall and ratchet notches provided at its outer wall facing the first member and extending in the axial direction, wherein the first member comprises a wall having an engagement member, which cooperates with the ratchet notches for adjusting the overall height of the spacer, and wherein the second member 84 has a window 85 therein for inserting graft material therethrough.

In cages of the present invention characterized as tall (greater than 40 mm), one annulus has a flange. Now referring to FIG. 1c, there is provided a cage of the present invention having features substantially the same as that of FIGS. 1a and 1b, except that the proximal portion of the inner second annulus has a distal flange 87 upon its inner end portion 88.

In some embodiments, the features of the engagement mechanism are reversed so that the pressure plate is located on the distal portion of the inner second annulus and the notches are located on the inner portion of the outer first annulus.

Figure 6:
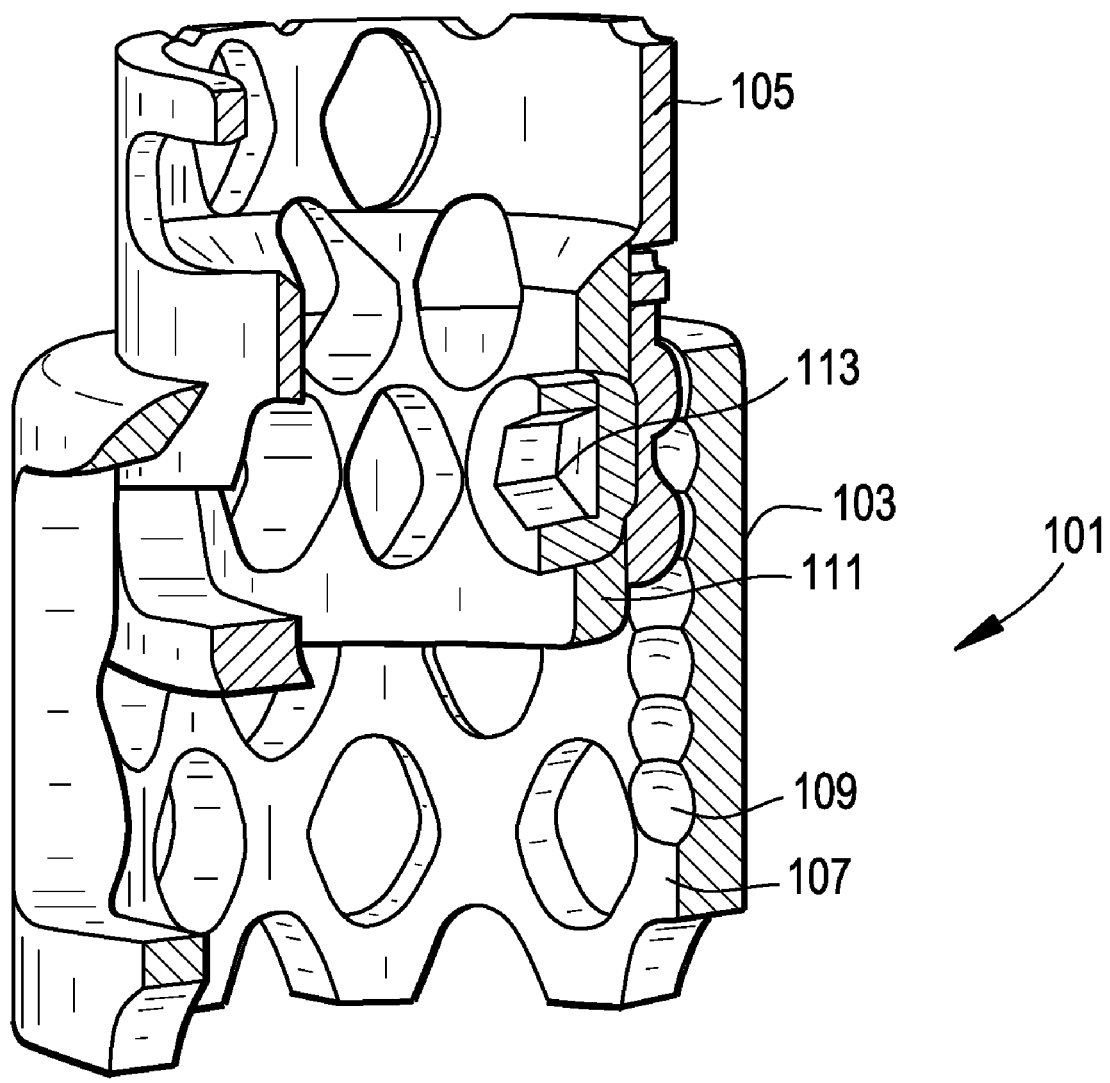
FIG. 6 discloses a cage of the present invention wherein the engagement mechanism comprises a pressure plate located on the distal portion of the inner second annulus and the notches located on the inner portion of the outer first annulus.

Now referring to FIG. 6, there is provided a spacer 101 for insertion between two vertebrae, the spacer having a variable axial height and comprising a sleeve-shaped first outer member 103 and a second inner member 105 guided within the first member to be slidable relative thereto in an axial direction thereof for adjusting an overall height, wherein the first outer member comprises an inner wall 107 and ratchet notches 109 provided at its inner wall facing the second member and extending in the axial direction, and wherein the second inner member comprises a wall 111 having an engagement member 113, which cooperates with the ratchet notches of the first outer member for adjusting the overall height of the spacer, and wherein the engagement member comprises i) a set screw and ii) a pressure plate having an outer face contacting the set screw and an inner face having teeth adapted to mate with the ratchet notches of the first outer member.

Instruments

In some embodiments, the instrument set used to implant the cage of the present invention includes a) a pistol grip inserter/expander; b) a secondary distractor; c) endplate trials (straight and flexible); d) a bone graft loading block; e) bone tamps; f) a 3 Nm torque limiting driver; g) a grabber/anti-torque instrument; and h) positioning impactors.

(Inserter-Expander Instrument)

Conventional inserters for expandable cages are beset with a number of challenges. First, if the cage is a threaded design, the inserter does not allow for rapid expansion of the implant. Second, conventional expanders do not provide significant tactile feedback of the distraction of the vertebral bodies. Third, if the cage requires rapid expansion, there is generally not an option for a secondary method of expansion for expansion of smaller increments. Fourth, there is no ability to rotate the handle to provide for easier viewing into the spine.

Now referring to FIG. 7, there is provided an inserter-expander instrument 115. This instrument is used to hold the cage during its insertion and expand the cage after it has been inserted. This instrument includes a modular inserter valve 117 for each size of implant; threaded pins 119 adapted for alignment of the cage and a third threaded rod (not shown) for attachment to the cage; a knob 121 for securing implant attachment to the inserter; a handle 123; and a knob 125 for expanding and retracting the cage. Also shown is a stand alone torque driver 124.

In use, the cage of the present invention is attached to the pins 119 by the surgeon using knob 121. Next, the cage is inserted into the implant site. Knob 125 is then rotated to expand the implant to the pre-determined height. Next, the cage height is locked by advancing the set screw of the engagement member. Lastly, knob 121 is then rotated to release the pins from the implant.

Figure 8A:
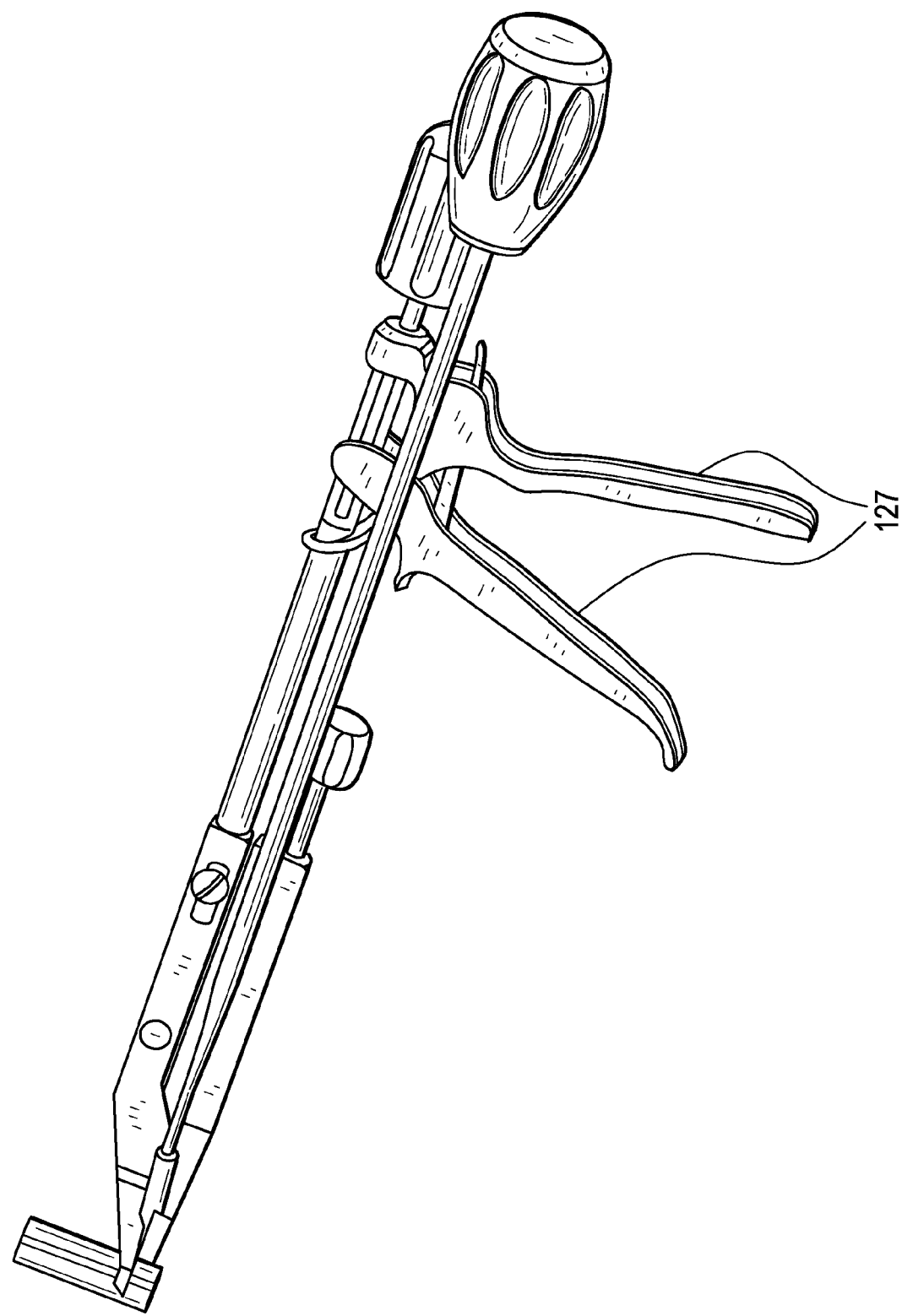
FIG. 8a discloses an inserter/expander instrument provided with a pistol grip

Now referring to FIG. 8a, in some embodiments, the inserter/expander instrument is provided with a pistol grip 127. The pistol grip provides an advantage in that it provides rapid implant expansion to contact the vertebral endplate.

Now referring to FIG. 8b, there is provided the inserter/expander instrument of FIG. 8a now shown in an expanded position. The inserter/expander instrument comprises:
a) a first, upper longitudinal member 501 having a distal end portion 503 adapted for engaging a first vertebral surface, an intermediate portion 505, and a proximal portion 507,
b) a second, lower longitudinal member 511 having a distal end portion 513 adapted for engaging a second vertebral surface, and an intermediate portion 515,
c) first 517 and second 519 cross bars distally pivotally attached to the longitudinal members at distal pivots 521; pivotally attached together at a third pivot 523; and slidably attached at their respective proximal ends to the opposing longitudinal member by a pin and groove arrangement 525,
d) a first expansion actuation mechanism 527 attached to the proximal portion of the upper longitudinal member, the expansion actuation mechanism adapted to incrementally distally advance the proximal portion first cross bar to expand the distal portions of the longitudinal members.

In the FIG. 8b, the expansion actuation mechanism 527 comprises a pistol grip 529 having a handle 531 attached to the upper longitudinal member, a pivotable lever 533 pivotally attached to the handle, and pivotally attached to the upper longitudinal member at a location 535 distal of the handle. The distal end 537 of the lever is pivotally attached to a flange 539 extending from a shaft 541 slidably movable in the cannulated proximal portion 507 of the upper longitudinal member. In use, gripping the lever results in a distal movement of the shaft 541. Because the distal end of the tube is connected to the pin of the pin and groove arrangement, distal movement of the tube results in an opening of the cross bars, and hence of opening of the distal end portions adapted for engaging a first vertebral surface ("the distal tips").

In some embodiments (not shown), the first expansion actuation mechanism can be a ratchet and pawl advancement mechanism, which can comprise:

i) a ratchet wheel having a centerpin pivotally attached to the housing proximal to the grip, and a circumference having a second plurality of teeth formed thereon shaped to engage the first plurality of teeth, ii) a lever having a first end portion pivotally attached to the ratchet wheel centerpin and a second end portion having a shape adapted for gripping, and having an outer surface having a pin extending therefrom, and iii) a pawl having a first end pivotally attached to the pin of the lever and a second end shaped for engaging the second plurality of teeth.

Any conventional means for incrementally expanding the distal tips may be used as the first expansion actuation mechanism. Generally, these are based upon advancing the shaft located within the cannulated proximal portion of the upper longitudinal member. In some embodiments, a ratchet and pawl mechanism is selected. In others, the advancement mechanism comprises a rack and pinion mechanism (such as a crank). In others, the advancement mechanism comprises a friction-based mechanism and a leaf spring. In others, the advancement mechanism comprises a tension band wound with a pulley that is wound in.

Preferably, the inserter-expander also has a second expansion actuation mechanism attached to the proximal portion of the first longitudinal member and adapted for fine tuning the expansion of the distal tips. Preferably, and now referring to FIG. 8b, this is accomplished by provided a threaded knob 545 that is threadably attached to the proximal end of the threaded tube housed within the cannulated proximal portion of the upper longitudinal member. Because the thread on the internal diameter of the tube and the thread on the outer diameter of the shaft of the knob are mating threads, turning the knob in a clockwise direction advances the distal end of the shaft of the knob. Because the proximal end of the shaft 549 of the knob is connected to the pin of the pin and groove arrangement, distal movement of the shaft of the knob results in an opening of the cross bars, and hence of opening of the distal end portions adapted for engaging a first vertebral surface ("the distal tips").

Thus, the fine tuning mechanism comprises:

a second expansion actuation mechanism attached to the proximal portion of the first longitudinal member, the second expansion actuation mechanism adapted to incrementally distally advance the proximal portion of the second cross bar to expand the distal portions of the longitudinal members.

Preferably, the second expansion actuation mechanism comprises a knob 545 having a threaded shaft 549 extending distally therefrom.

Figure 9C:
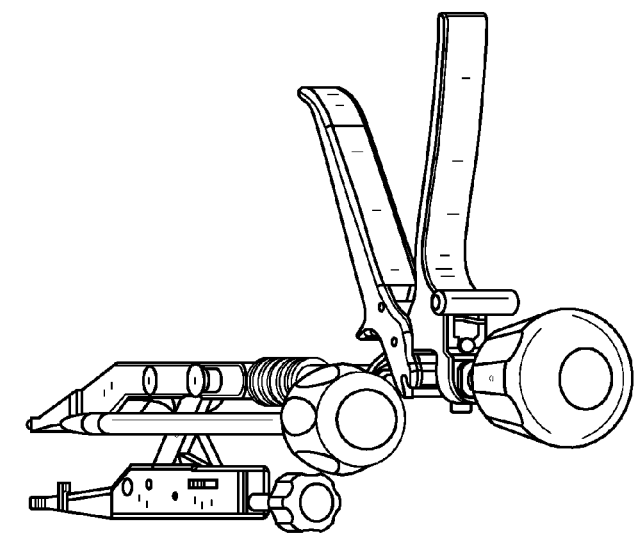
FIG. 9d discloses a closeup of the guide and safety components on the distal tips.
FIG. 9e discloses a closeup of the safety flange component of the inserter-expander.
FIG. 9f discloses a closeup of the location of the spring component of the inserter-expander.
FIG. 9g discloses a closeup of the modular arms and associated push button components of the inserter-expander.
FIG. 9h discloses a closeup of the dual ratchet mechanism with offset components of the inserter-expander.
Figure 9B:
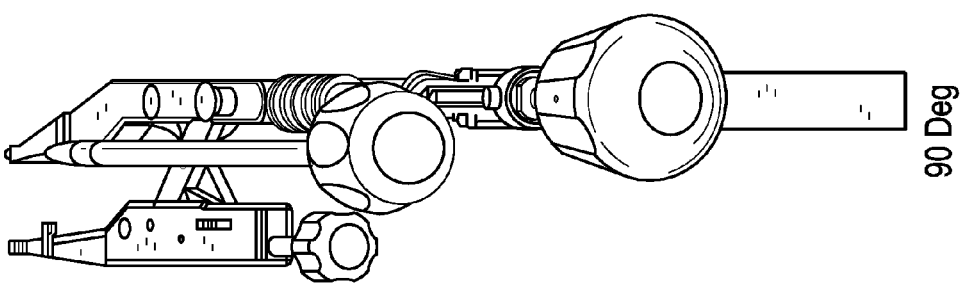
Figure 9A:
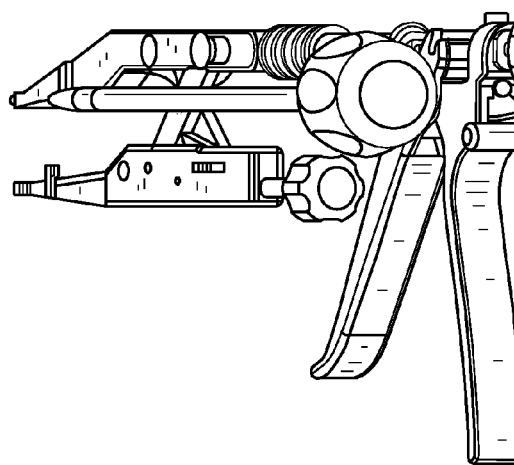

Now referring to FIG. 9a-9c, the pistol grip portion of the instrument can be adapted to provide rotation. This pistol grip can rotate and then lock into one of three positions. FIG. 9a shows the pistol grip in the 0 degree position. FIG. 9b shows the pistol grip in the 90 degree position. FIG. 9c shows the pistol grip in the 180 degree position. Now referring back to FIG. 8b, preferably, locking of the rotatable pistol grip is accomplished by a locking sleeve 551.

Figure 9D:
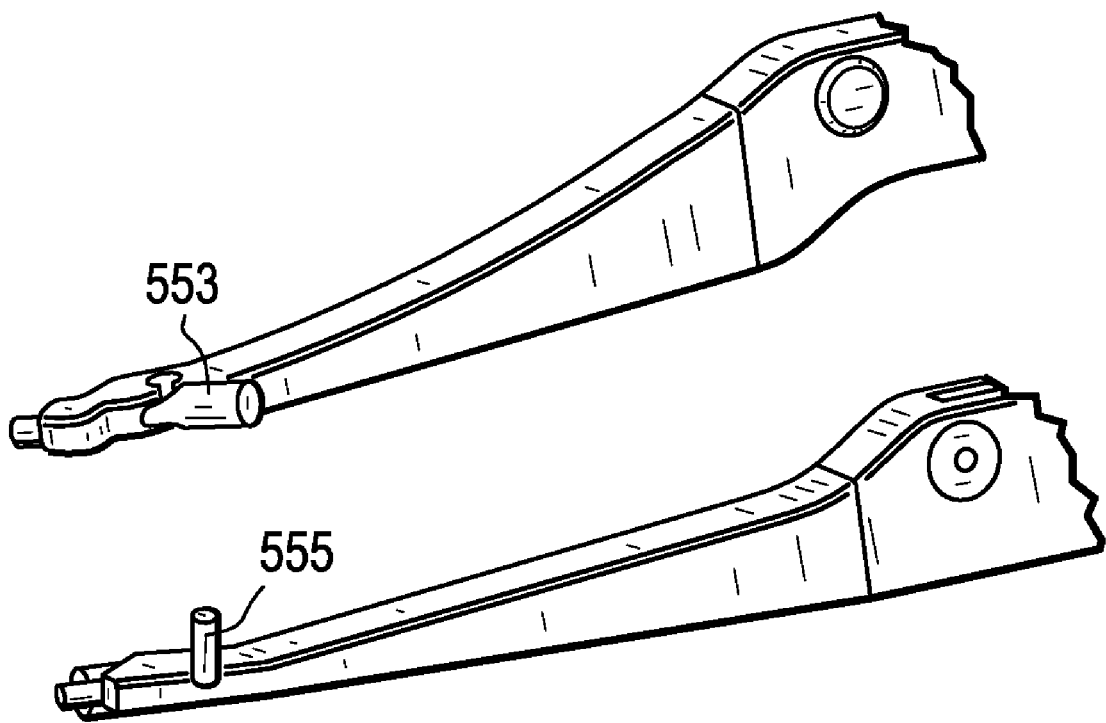

Now referring to FIG. 9d, there are provided a guide and a safety respectively located near the distal tips of the upper and lower longitudinal members. The guide 553 is for reception of a torque-limiting driver that can lock the expandable implant once the desired height of the implant has been attained. The safety 555 prevents use of the torque driver if the implant has not been expanded 5 mm. Accordingly, the safety prevents an unacceptably short implant from being locked on top of the graft window.

Figure 9E:
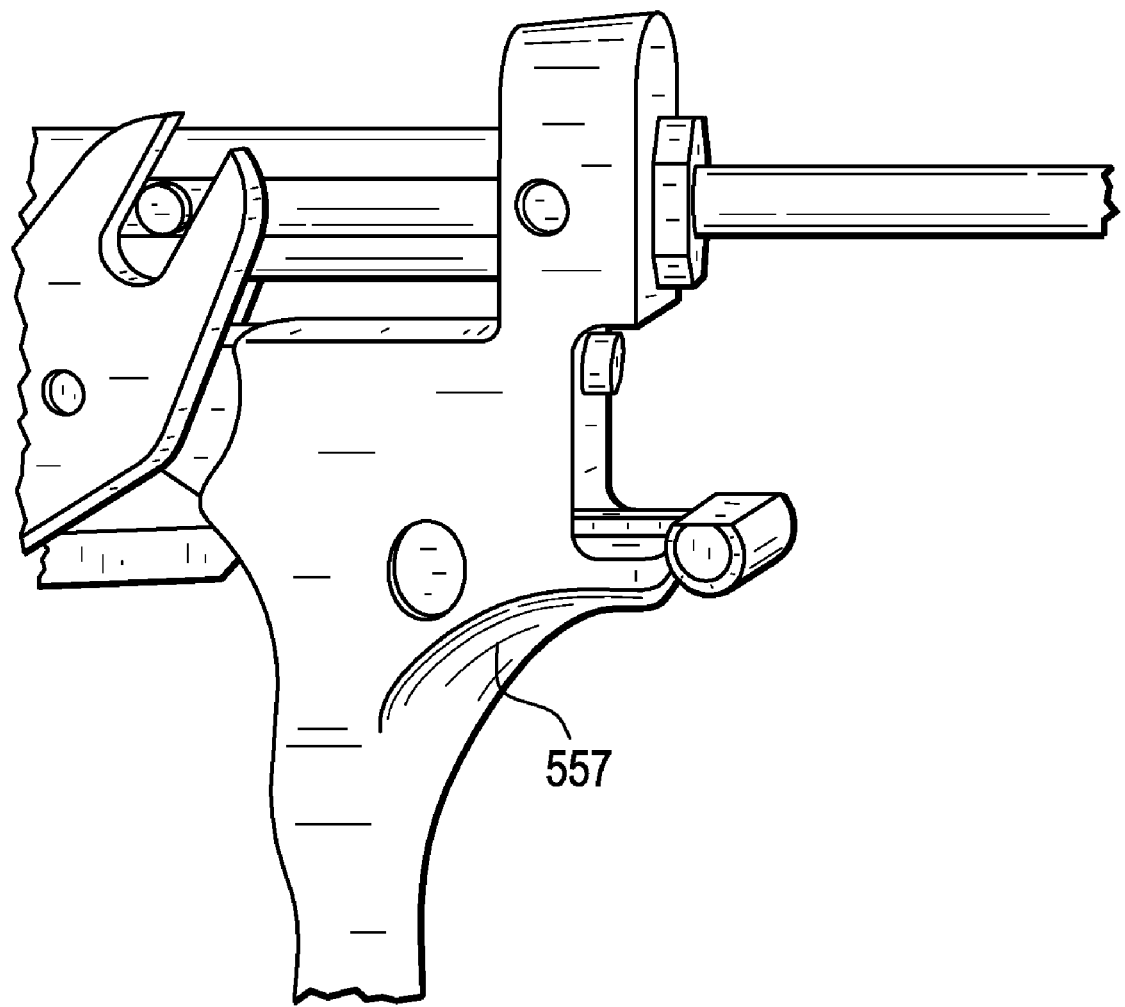

Now referring to FIG. 9e, the inserter/expander also has another safety flange 557 located on a proximal portion of the handle, which protects the user from catching gloves or skin during the ratchet lock release.

Now referring back to FIG. 8b, the inserter/expander also has a push button 559, which when depressed, releases the ratchet mechanism actuated by the pistol grip that holds the implant extended. Now referring to FIG. 9f, the inserter/expander also has a spring 560 located within the cannulated upper longitudinal member that provides natural retraction of the pistol grip when the push button is depressed.

Now referring back to FIG. 8b, the inserter/expander also has a locking handle 561 extending through the lower longitudinal member that threads the implant to the distal tips of the inserter/expander. In this particular embodiment, the locking handle comprises a knob 563 having a shaft 565 that extends to the distal tips.

Figure 9G:
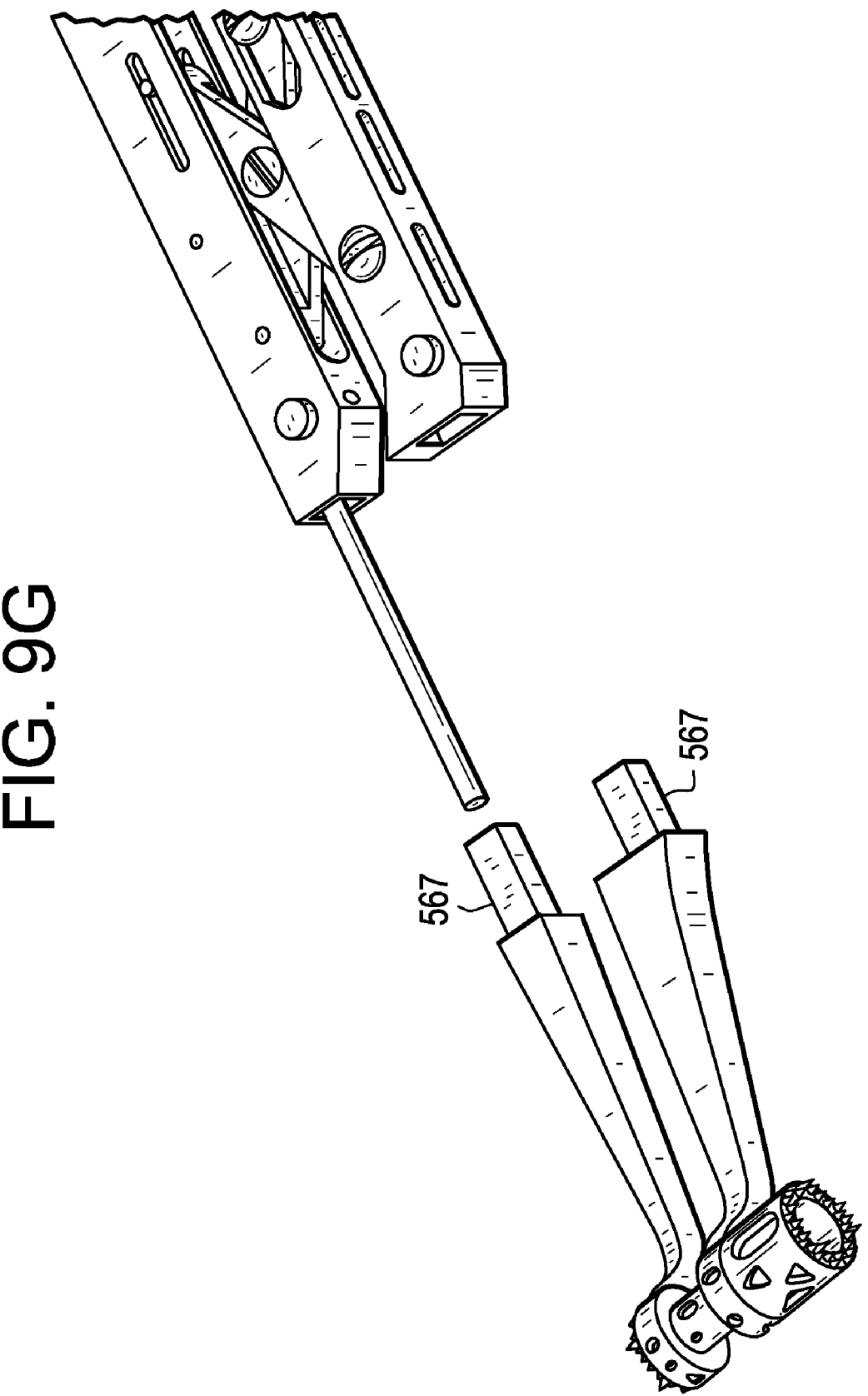

Now referring to FIG. 9g, the inserter/expander also has modular arms 567. The detachability of these arms allows the surgeon to accommodate different implant sizes and to easily detach the main body of the inserter/expander from these arms, thereby allowing x-rays to be easily taken. Push buttons 569 located on the inserter/expander main body allow the surgeon to unlock these modular arms from the main body.

Figure 9H:
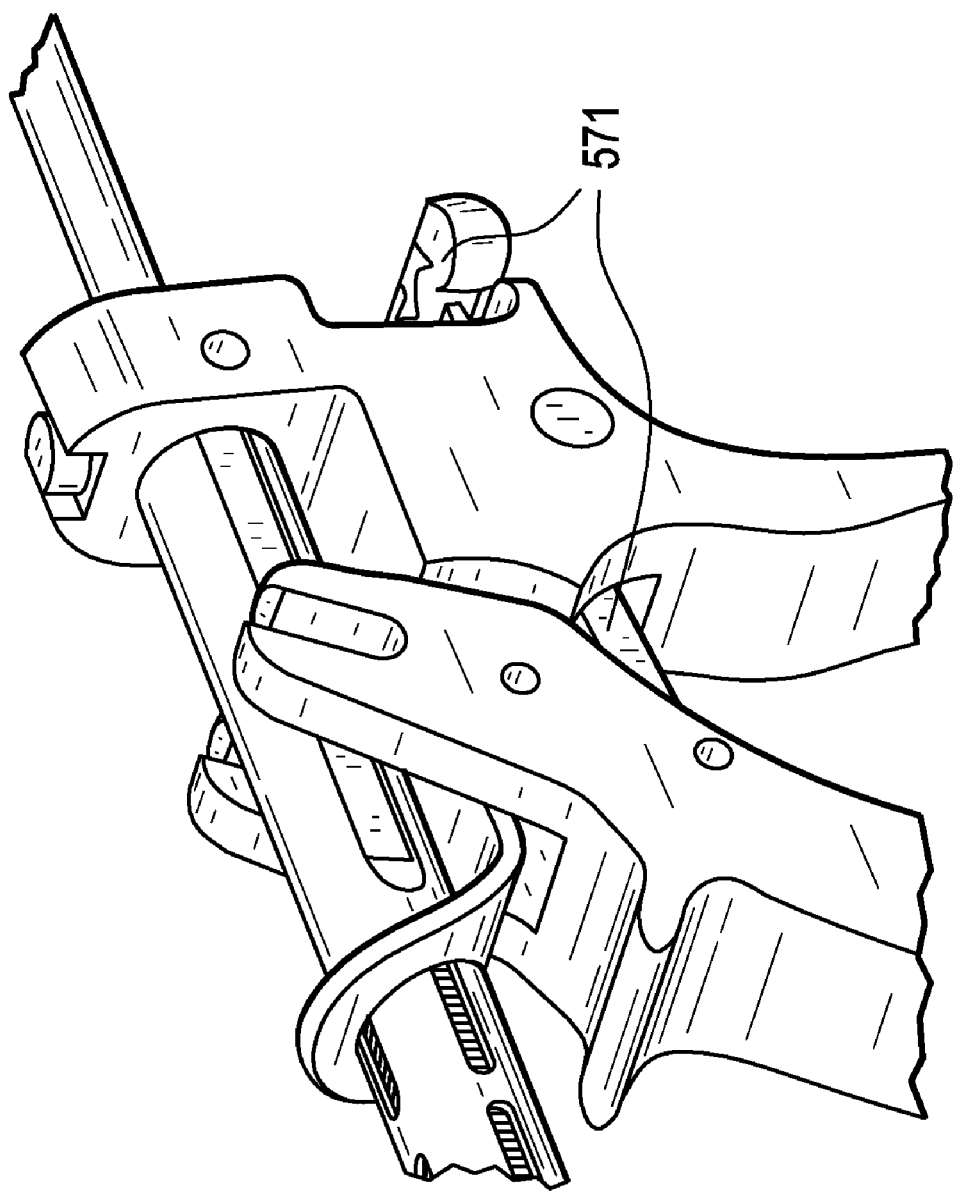

Now referring to FIG. 9h, the inserter/expander also has a dual ratchet mechanism 571 with offset, which can provide smaller incremental steps of expansion.

The current invention allows for a) a primary method of rapid expansion using an ergonomic pistol grip design and b) a secondary method of expansion for expanding a vertebral body replacement with smaller height increments to optimize the patient fit. The pistol grip design also provides tactile feedback to the physician as to the distraction force placed on the spine as the implant expands. In addition, the tips of the inserter/expander may be modular to attach to different sized implants and also accommodate different surgical approaches where different angles to the main body are required.

Therefore, there are a number of advantages of the inserter/expander of the present invention. First, it provides two methods of expanding the implant within the same instrument. Second, the instrument design provides for both for a) rapid, large increment expansion and b) small, fine tuning increment expansion. Third, the instrument has an ergonomic pistol grip. Fourth, the instrument has a three-position pistol grip for maximum ergonomics. Fourth, it has a guide for a set screw tightener. Fifth, it has modular tips to accommodate different surgical approaches (posterior, anterolateral, etc). Sixth, it has modular tips designed to custom fit different implant sizes. Seventh, it has an integrated safety feature to ensure that locking mechanism is not allowed below a minimum distraction.

Figure 10A:
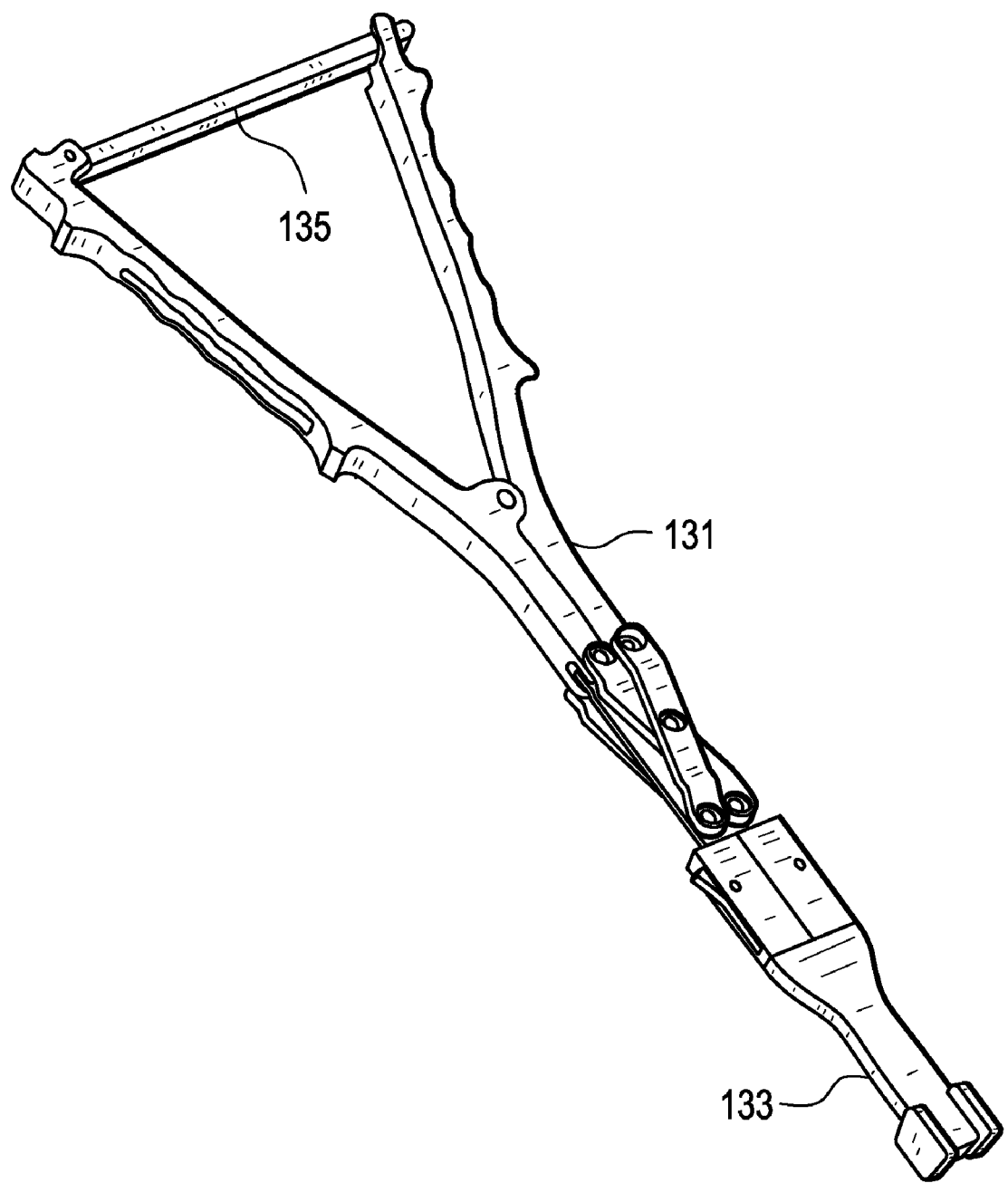
Figure 10B:
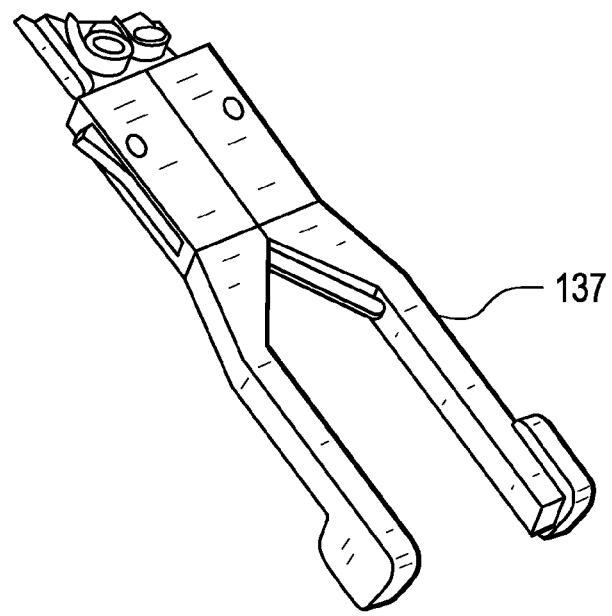
Figure 10C:
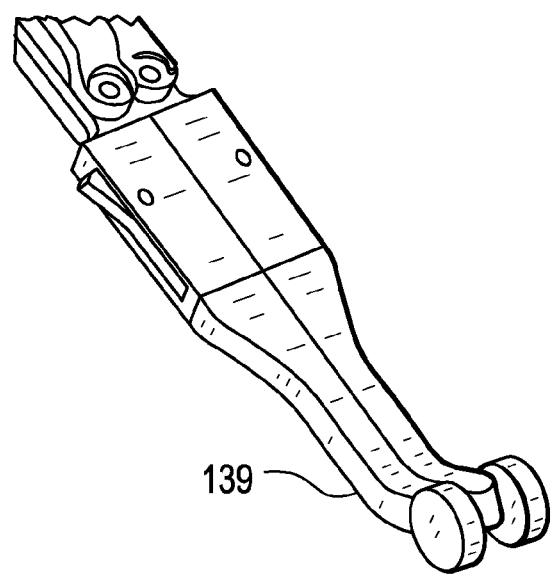

Now referring to FIGS. 10a-10c, there are provided figures of the second distractor 131. The function of the second distractor is to first distract the vertebral bodies located above and below the implantation site to their normal anatomical position and then to estimate the size of the implant required. FIG. 10a shows the secondary distractor with lateral attachments 133 and a height indicator 135. FIGS. 10b and 10c provide closeups of the distal end of the secondary distractor having offset lateral attachments 137 (to estimate height for taller implants) and angled posterior attachments 139 (for ease of use during posterior surgical approaches).

FIG. 10b provides a closeup of the distal tip of a first preferred secondary distractor having a laterally offset tip 137. This tip, which preferably is provided in a modular form, can be suitably used to estimate the intraspinous space for taller implants.

FIG. 10c provides a closeup of the distal tip of a second preferred secondary distractor having a laterally offset tip 139 to be used during posterior surgical approaches.

Figure 10D:
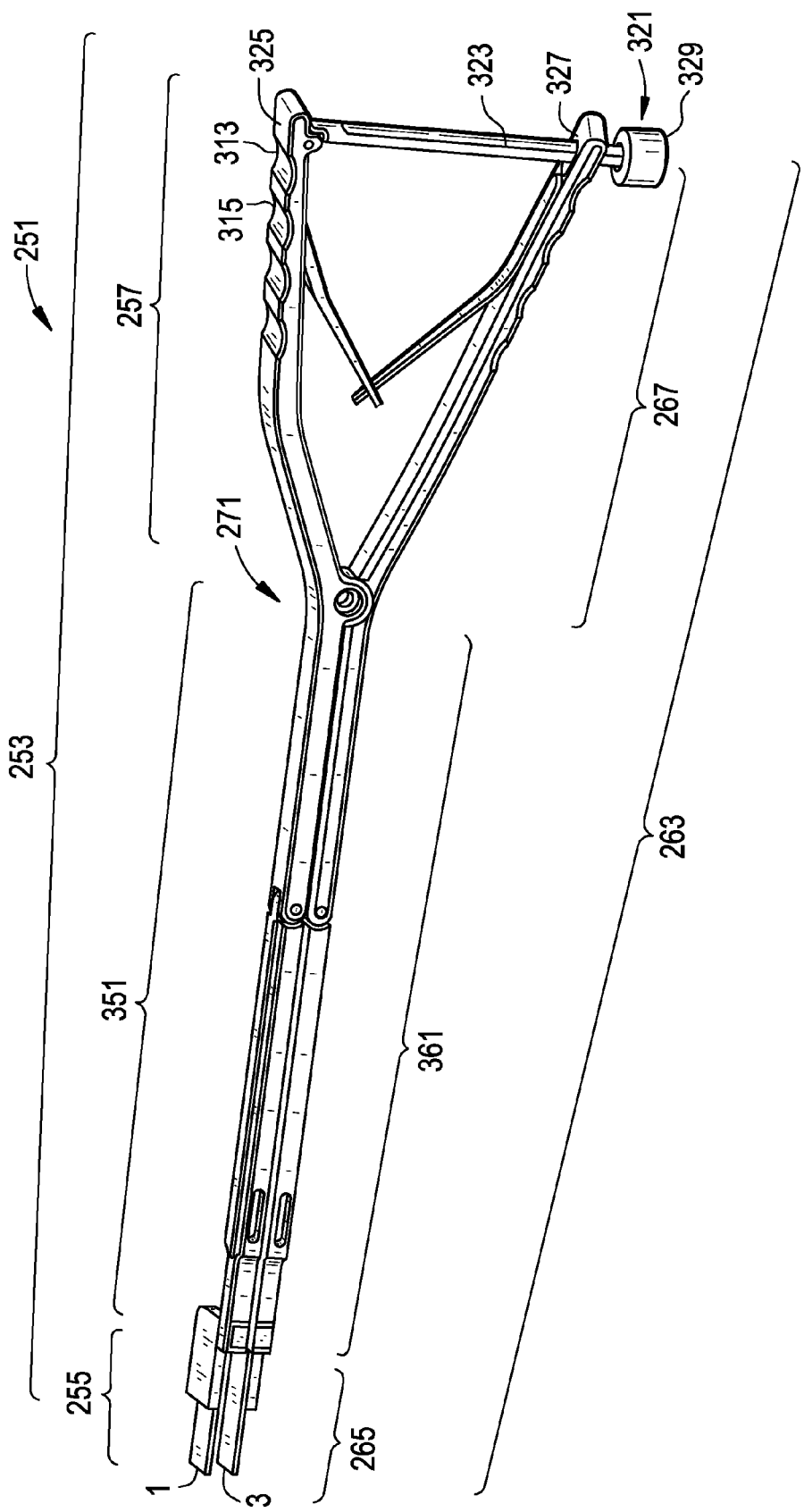

Now therefore, in accordance with the present invention, and now referring to FIG. 10d, there is provided a distractor 251 for distracting an intervertebral disc space, comprising:
a) a first longitudinal member 253 having a distal end portion 255 adapted for engaging a first vertebral surface, an intermediate portion 351, and a proximal handle portion 257,
b) a second longitudinal member 263 having a distal end portion 265 adapted for engaging a second vertebral surface, an intermediate portion 361, and a proximal handle portion 267,
the first and second longitudinal members being pivotally attached at a pivot junction 271 between the proximal handle and intermediate portions of each longitudinal member,
c) a height indicator 321 is also disposed at least partially between handle portions of the longitudinal members and adapted to report a height corresponding to a change in distance between the attachment points of the proximal handle portions.

In some embodiments, the distal end portions of the distractor comprises distal tips 281,283. The distal tips of the distractor are adapted to enter the disc space and then distract the disc space by moving apart. Accordingly, the combined thickness of the distal tips should be as small as possible. The tips should be made of material strong enough to withstand the resisting forces of the supporting structures. The outer surfaces of the distal tips are preferably sufficiently smooth to avoid damaging the opposing vertebral walls.

In some embodiments, at least one of the distal end portions also comprises a proximally-positioned stops 285, which are designed to abut the front wall of at least one of the opposing vertebral bodies and prevent the surgeon from proceeding too far into the disc space.

Preferably, these intermediate portions have a long length (e.g., at least 10 times the length of the corresponding distal tip) sufficient to extend into the patient's body cavity, thereby allowing its use in anterior approach procedures.

In some embodiments, the intermediate portion of the longitudinal member consists essentially of a substantially rigid portion. This has the advantage of manufacturing simplicity.

Figure 10E:
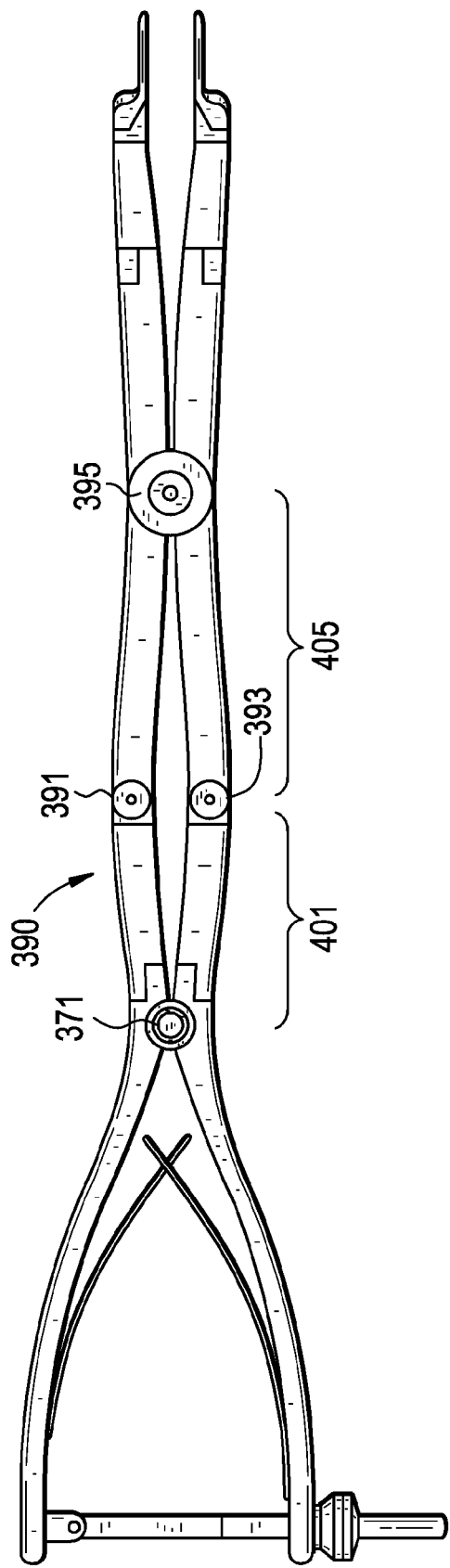

In other embodiments, as in FIG. 10e, the intermediate portion of each member form a double action pivot 390 comprising second 391 and third 393 pivots, and a fourth pivot 395 distal to the double action pivot, thereby defining proximal 401 and distal 405 portions of the intermediate portion. In the embodiment of FIG. 10e, when the proximal handle portions are squeezed together, first pivot 371 causes a distal widening of the proximal portions of the intermediate portions, the double action pivot arrests the distal widening between the distal portions of the intermediate portions, and the fourth pivot causes a distal widening of the distal portions of the device. Because the double action pivot arrests the distal widening, it helps reduce the distance between the distal tips when the proximal handles are squeezed together. Since large distance changes between the proximal handles causes small distance changes between the tips, this device provides both mechanical advantage and sensitivity.

In the embodiment of FIG. 10f, there is provided first and second cross bars 341,143 proximally pivotally attached to the longitudinal members at the proximal pivots 291,293; pivotally attached together at a fourth pivot 295; and slidably attached at their respective distal ends 345, 347 to the opposing longitudinal member by a pin and groove arrangement. This parallel action embodiment has the advantage of producing parallel distal portions when the handles are squeezed together.

The junction of the proximal handle and intermediate portions of each longitudinal member is adapted to accommodate a first pivot for pivotally attaching the longitudinal members. Preferably, the junction is located from the proximal handle end of the device a distance of between about 10-50% of the overall length of the device.

The first pivot is located at the junction between the intermediate and proximal handle portions of the longitudinal members and is adapted to effectively transmit force therebetween to open or close the more distal portions longitudinal members without causing deleterious jamming. In some embodiments, the first pivot is adapted so that, when the proximal handles are squeezed together, there is a narrowing of the longitudinal members. In other embodiments, the first pivot is adapted so that, when the proximal handles are squeezed together, there is a widening of the longitudinal members.

Typically, the proximal handle portions of each longitudinal member are adapted to produce a force to be transmitted distally when the proximal handle portions are moved either towards each other (in some instances) or away from each other (in some instances). Preferably, these proximal handle portions have a long length (e.g., at least 5 times the length of the corresponding distal tip) sufficient to extend into the patient's body cavity, thereby allowing its use in anterior approach procedures.

In some embodiments, the proximal handle portion consists essentially of a substantially straight beam portion. This has the advantage of simplicity in manufacturing.

In preferred embodiments, the proximal portion of the handle portion has a surface 313 compatible for gripping by the surgeon. In some embodiments, these gripping surfaces are disposed on the outer facing surfaces 315 of the proximal portions of the handle portions.

In some embodiments of the present invention, a height indicator 321 is also disposed at least partially between handle portions of the longitudinal members. It typically comprises a graduated beam 323 pivotally attached to a proximal portion 325 of a first handle portion and positioned to slide through a through hole 327 positioned on a proximal portion of a second handle portion. Prior experimentation has determined the relationship between the displacement of the two connection points (of the height indicator) and the displacement between the two distal tips (which produce distraction). Thus, when the device is used and the distance between the connection points changes, the height indicator can report the corresponding distance between the distal tips by providing that corresponding distance on the graduated beam adjacent the through hole. Typically, the height indicator also has a stop 329 disposed at its unconnected end.

Typically, the components of the present invention can be made out of any material commonly used in medical instruments. If the device is designed to be reusable, then it is preferred that all the components be made of stainless steel. If the device is designed to be disposable, then it is preferred that some of the components be made of plastic. Preferably, at least one component is sterilized. More preferably, each component is sterilized.

In preferred embodiments, as in FIG. 10f, the proximal handle portion and the proximal portion of the intermediate section are made of a first single piece, while the distal portion of the intermediate portion and the distal portion of the device are made of a second single piece. In this embodiment, all of the portions of the first longitudinal member are disposed on the upper portion of the device.

In other embodiments, as in FIG. 10e (FIG. 3—DEP0809), the second single piece is shaped so as to cross over the fourth pivot, so that the first longitudinal member comprises the upper proximal handle, the upper intermediate portion, and the lower distal portion.

Typically, the thickness and spacing of the distal tips are predetermined to fit snugly within a typical collapsed disc space. In this condition, the first change in distance between the distracting tips produces a corresponding change in the height of the disc space. However, if the tips are undersized (i.e., the tips are relatively small so that their initial distraction does not distract the disc space, but only causes initial contact with the opposed endplates), the force required to make this initial contact should be substracted from the ultimate force measurement.

Figure 11:
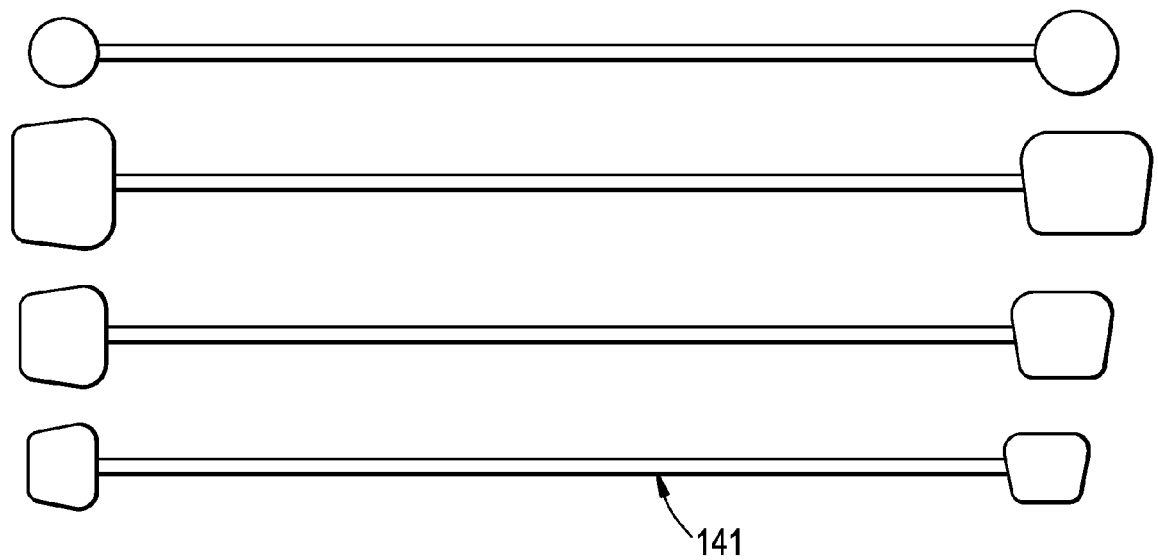
FIG. 11 discloses a plurality of endplate trials used with a posterior approach cage.

Now referring to FIG. 11, there is provided a plurality of endplate trials 141 used with a posterior approach cage. These trials are used to assess the dimensions of the vertebral endplates against which the cage will seat in order to select the appropriate size for an endplate of the cage of the present invention. These trials can be made with varying levels of flexibility in order to allow access around the local tissue and to access the exposed vertebral body endplate.

Figure 12:
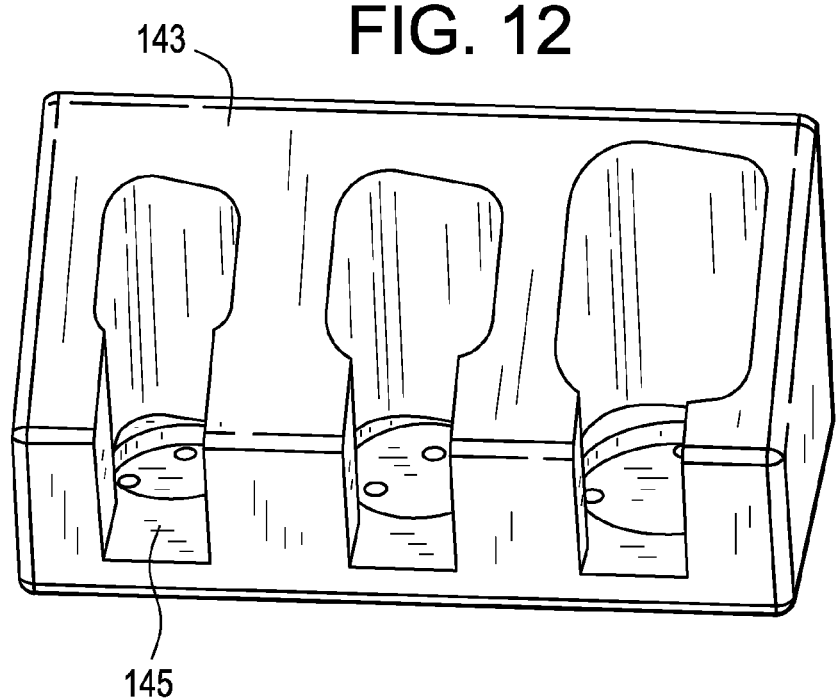
FIG. 12 discloses a graft loading block.

Now referring to FIG. 12, there is provided a graft loading block 143 having a plurality of recesses 145 conforming to the shapes of various size cages. The surgeon puts the cage into this block during graft loading in order to enhance the stability of the loading procedure.

Figure 13:
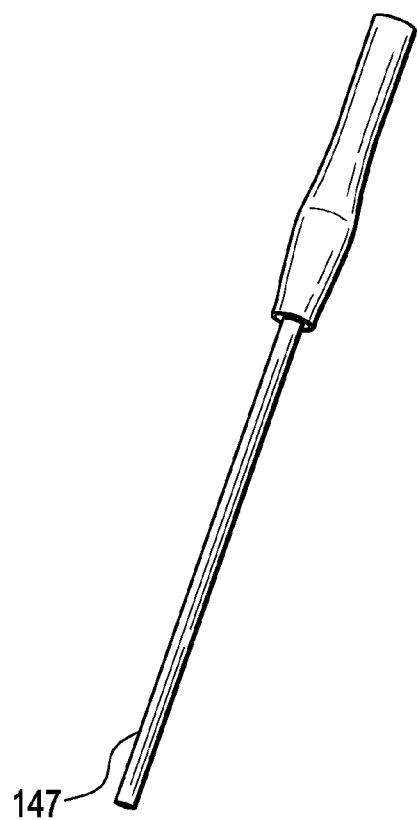
FIG. 13 discloses a bone tamp.

Now referring to FIG. 13, there is provided a bone tamp 147, which is used to pack the bone graft into the cage after it has been loaded into the cage.

Figure 14:
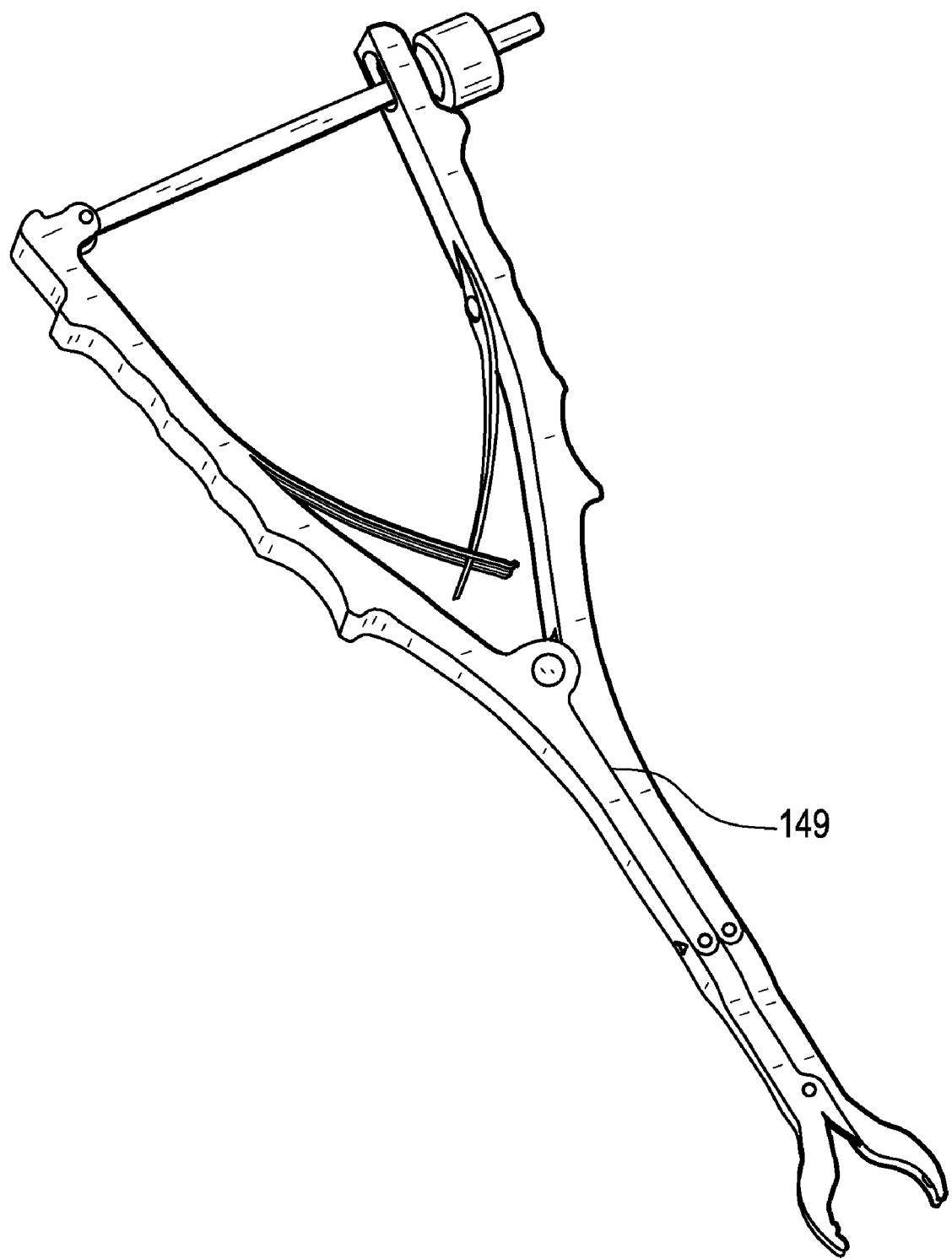
FIG. 14 discloses a grabber anti-torque instrument.

Now referring to FIG. 14, there is provided a grabber anti-torque instrument 149. The function of the grabber anti-torque instrument is to stabilize the implant when the set screw is loosened for retraction and to remove the implant from the site.

Figure 15A:
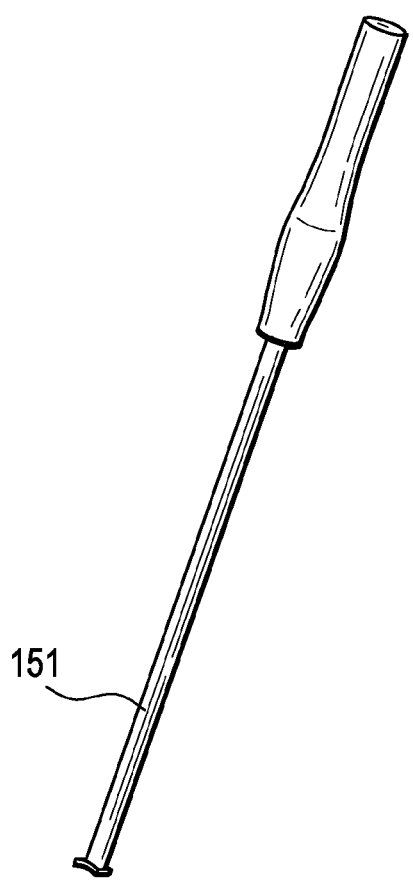
FIG. 15 discloses a pair of positioning impactors.
Figure 15B:
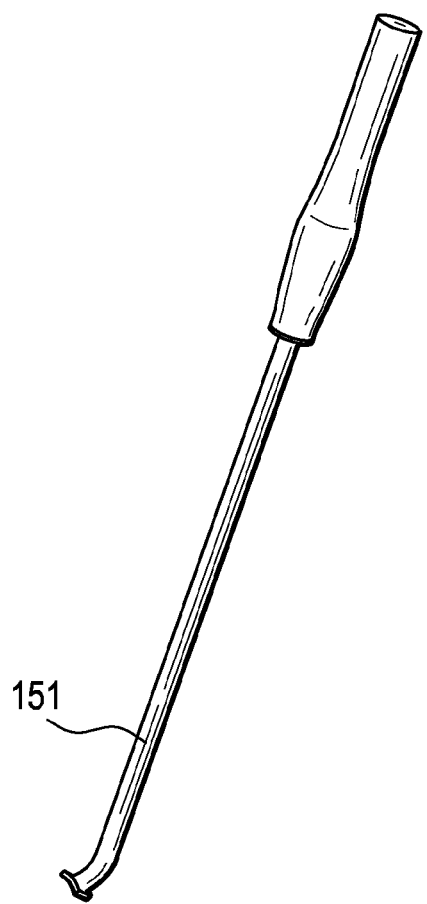

Now referring to FIGS. 15a and 15b, there is provided a pair of positioning impactors 151. These instruments may be used to gently reposition the implant.

In some embodiments, the graft window of the present invention is used to a deliver either a bone cement or a bone-forming agent into the cage. The bone cement may be any material typically used to augment vertebral bodies, including acrylic-based bone cements (such as PMMA-based bone cements), pastes comprising bone particles (either mineralized or demineralized or both; and ceramic-based bone cements (such as HA and TCP-based pastes). In some embodiments, the bone cement comprises the bone cement disclosed in WO 02/064062 (Voellmicke).

For the purposes of the present invention, the terms "bone-forming agent" and "bone growth agent" are used interchangeably. Typically, the bone-forming agent may be:

a) a growth factor (such as an osteoinductive or angiogenic factor),
b) osteoconductive (such as a porous matrix of granules),
c) osteogenic (such as viable osteoprogenitor cells), or
d) plasmid DNA.

In some embodiments, the formulation comprises a liquid carrier, and the bone forming agent is soluble in the carrier.

In some embodiments, the bone forming agent is a growth factor. As used herein, the term "growth factor" encompasses any cellular product that modulates the growth or differentiation of other cells, particularly connective tissue progenitor cells. The growth factors that may be used in accordance with the present invention include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-β superfamily, including TGF-β1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including MP-52; HBGF-1 and HBGF-2; growth differentiation factors (GDFs), including GDF-5, members of the hedgehog family of proteins, including indian, sonic and desert hedgehog; ADMP-1; bone-forming members of the interleukin (IL) family; GDF-5; and members of the colony-stimulating factor (CSF) family, including CSF-1, G-CSF, and GM-CSF; and isoforms thereof.

In some embodiments, the growth factor is selected from the group consisting of TGF-β, bFGF, and IGF-1. These growth factors are believed to promote the regeneration of bone. In some embodiments, the growth factor is TGF-β. More preferably, TGF-β is administered in an amount of between about 10 ng/ml and about 5000 ng/ml, for example, between about 50 ng/ml and about 500 ng/ml, e.g., between about 100 ng/ml and about 300 ng/ml.

In some embodiments, platelet concentrate is provided as the bone forming agent. In one embodiment, the growth factors released by the platelets are present in an amount at least two-fold (e.g., four-fold) greater than the amount found in the blood from which the platelets were taken. In some embodiments, the platelet concentrate is autologous. In some embodiments, the platelet concentrate is platelet rich plasma (PRP). PRP is advantageous because it contains growth factors that can restimulate the growth of the bone, and because its fibrin matrix provides a suitable scaffold for new tissue growth.

In some embodiments, the bone forming agent comprises an effective amount of a bone morphogenic protein (BMP). BMPs beneficially increasing bone formation by promoting the differentiation of mesenchymal stem cells (MSCs) into osteoblasts and their proliferation.

In some embodiments, between about 1 ng and about 10 mg of BMP are intraosseously administered into the target bone. In some embodiments, between about 1 microgram (μg) and about 1 mg of BMP are intraosseously administered into the target bone.

In some embodiments, the bone forming agent comprises an effective amount of a fibroblast growth factor (FGF). FGF is a potent mitogen and is angiogenic, and so attracts mesenchymal stem cells to the target area. It is further believed that FGF stimulates osteoblasts to differentiate into osteocytes.

In some embodiments, the FGF is acidic FGF (aFGF).
In some embodiments, the FGF is basic FGF (bFGF).
In some embodiments, between about 1 microgram (μg) and about 10,000 μg of FGF are intraosseously administered into the target bone. In some embodiments, between about 10 μg and about 1,000 μg of FGF are intraosseously administered into the target bone. In some embodiments, between about 50 μg and about 600 μg of FGF are intraosseously administered into the target bone.

In some embodiments, between about 0.1 and about 4 mg/kg/day of FGF are intraosseously administered into the target bone. In some embodiments, between about 1 and about 2 mg/kg/day of FGF are intraosseously administered into the target bone.

In some embodiments, FGF is intraosseously administered into the target bone in a concentration of between about 0.1 mg/ml and about 100 mg/ml. In some embodiments, FGF is intraosseously administered into the target bone in a concentration of between about 0.5 mg/ml and about 30 mg/ml. In some embodiments, FGF is intraosseously administered into the target bone in a concentration of between about 1 mg/ml and about 10 mg/ml.

In some embodiments, FGF is intraosseously administered into the target bone in an amount to provide a local tissue concentration of between about 0.1 mg/kg and about 10 mg/kg.

In some embodiments, the formulation comprises a hyaluronic acid carrier and bFGF. In some embodiments, formulations described in U.S. Pat. No. 5,942,499 ("Orquest") are selected as FGF-containing formulations.

In some embodiments, the bone forming agent comprises an effective amount of insulin-like growth factor. IGFs beneficially increase bone formation by promoting mitogenic activity and/or cell proliferation.

In some embodiments, the bone forming agent comprises an effective amount of parathyroid hormone (PTH). Without wishing to be tied to a theory, it is believed that PTH beneficially increases bone formation by mediating the proliferation of osteoblasts.

In some embodiments, the PTH is a fragment or variant, such as those taught in U.S. Pat. No. 5,510,370 (Hock) and U.S. Pat. No. 6,590,081 (Zhang), and published patent application 2002/0107200 (Chang), the entire contents of which are incorporated herein in their entirety. In one embodiment, the PTH is PTH (1-34) (teriparatide), e.g., FORTEO® (Eli Lilly and Company). In some embodiments, the BFA is a parathyroid hormone derivative, such as a parathyroid hormone mutein. Examples of parathyroid muteins are discussed in U.S. Pat. No. 5,856,138 (Fukuda), the entire contents of which are incorporated herein in its entirety.

In some embodiments, the bone forming agent comprises an effective amount of a statin. Without wishing to be tied to a theory, it is believed that statins beneficially increase bone formation by enhancing the expression of BMPs.

In some embodiments, the bone forming agent is a porous matrix, and is preferably injectable. In some embodiments, the porous matrix is a mineral. In one embodiment, this mineral comprises calcium and phosphorus. In some embodiments, the mineral is selected from the group consisting of calcium phosphate, tricalcium phosphate and hydroxyapatite. In one embodiment, the average porosity of the matrix is between about 20 and about 500 μm, for example, between about 50 and about 250 μm. In yet other embodiments of the present invention, in situ porosity is produced in the injected matrix to produce a porous scaffold in the injected fracture stabilizing cement. Once the in situ porosity is produced in the target tissue, the surgeon can inject other therapeutic compounds into the porosity, thereby treating the surrounding tissues and enhancing the remodeling process of the target tissue and the injectable cement.

In some embodiments, the mineral is administered in a granule form. It is believed that the administration of granular minerals promotes the formation of the bone growth around the minerals such that osteointegration occurs.

In some embodiments, the mineral is administered in a settable-paste form. In this condition, the paste sets up in vivo, and thereby immediately imparts post-treatment mechanical support to the fragile OP body.

In another embodiment, the treatment is delivered via injectable absorbable or non-absorbable cement to the target tissue. The treatment is formulated using bioabsorbable macro-sphere technologies, such that it will allow the release of the bone forming agent first, followed by the release of the anti-resorptive agent. The cement will provide the initial stability required to treat pain in fractured target tissues. These tissues include, but are not limited to, hips, knee, vertebral body fractures and iliac crest fractures. In some embodiments, the cement is selected from the group consisting of calcium phosphate, tricalcium phosphate and hydroxyapatite. In other embodiments, the cement is any hard biocompatible cement, including PMMA, processed autogenous and allograft bone. Hydroxylapatite is a preferred cement because of its strength and biological profile. Tricalcium phosphate may also be used alone or in combination with hydroxylapatite, particularly if some degree of resorption is desired in the cement.

In some embodiments, the porous matrix comprises a resorbable polymeric material.

In some embodiments, the bone forming agent comprises an injectable precursor fluid that produces the in situ formation of a mineralized collagen composite. In some embodiments, the injectable precursor fluid comprises:
 a) a first formulation comprising an acid-soluble type I collagen solution (preferably between about 1 mg/ml and about 7 mg/ml collagen) and
 b) a second formulation comprising liposomes containing calcium and phosphate.

Combining the acid-soluble collagen solution with the calcium- and phosphate-loaded liposomes results in a liposome/collagen precursor fluid, which, when heated from room temperature to 37° C., forms a mineralized collagen gel.

In some embodiments, the liposomes are loaded with dipalmitoylphosphatidylcholine (90 mol %) and dimyristoyl phosphatidylcholine (10 mol %). These liposomes are stable at room temperature but form calcium phosphate mineral when heated above 35° C., a consequence of the release of entrapped salts at the lipid chain melting transition. One such technology is disclosed in Pederson, *Biomaterials* 24: 4881-4890 (2003), the specification of which is incorporated herein by reference in its entirety.

Alternatively, the in situ mineralization of collagen could be achieved by an increase in temperature achieved by other types of reactions including, but not limited to, chemical, enzymatic, magnetic, electric, photo- or nuclear. Suitable sources thereof include light, chemical reaction, enzymatically controlled reaction and an electric wire embedded in the material. To further elucidate the electric wire approach, a wire (which can be the reinforcement rod) can first be embedded in the space, heated to create the calcium deposition, and then withdrawn. In some embodiments, this wire may be a shape memory such as nitinol that can form the shape. Alternatively, an electrically-conducting polymer can be selected as the temperature raising element. This polymer is heated to form the collagen, and is then subject to disintegration and resorption in situ, thereby providing space adjacent the mineralized collagen for the bone to form.

In one embodiment, the bone forming agent is a plurality of viable osteoprogenitor cells. Such viable cells, introduced into the bone, have the capability of at least partially repairing any bone loss experienced by the bone during the osteoporotic process. In some embodiments, these cells are introduced into the cancellous portion of the bone and ultimately produce new cancellous bone. In others, these cells are introduced into the cortical region and produce new cortical bone.

In some embodiments, these cells are obtained from another human individual (allograft), while in other embodiments, the cells are obtained from the same individual (autograft). In some embodiments, the cells are taken from bone tissue, while in others, the cells are taken from a non-bone tissue (and may, for example, be mesenchymal stem cells, chondrocytes or fibroblasts). In others, autograft osteocytes (such as from the knee, hip, shoulder, finger or ear) may be used.

In one embodiment, when viable cells are selected as an additional therapeutic agent or substance, the viable cells comprise mesenchymal stem cells (MSCs). MSCs provide a special advantage for administration into an uncoupled resorbing bone because it is believed that they can more readily survive the relatively harsh environment present in the uncoupled resorbing bone; that they have a desirable level of plasticity; and that they have the ability to proliferate and differentiate into the desired cells.

In some embodiments, the mesenchymal stem cells are obtained from bone marrow, such as autologous bone marrow. In others, the mesenchymal stem cells are obtained from adipose tissue, preferably autologous adipose tissue.

In some embodiments, the mesenchymal stem cells injected into the bone are provided in an unconcentrated form, e.g., from fresh bone marrow. In others, they are provided in a concentrated form. When provided in concentrated form, they can be uncultured. Uncultured, concentrated MSCs can be readily obtained by centrifugation, filtration, or immuno-absorption. When filtration is selected, the methods disclosed in U.S. Pat. No. 6,049,026 ("Muschler"), the specification of which is incorporated herein by reference in its entirety, can be used. In some embodiments, the matrix used to filter and concentrate the MSCs is also administered into the uncoupled resorbing bone.

In some embodiments, bone cells (which may be from either an allogeneic or an autologous source) or mesenchymal stem cells, may be genetically modified to produce an osteoinductive bone anabolic agent which could be chosen from the list of growth factors named herein. The production of these osteopromotive agents may lead to bone growth.

In some embodiments, the osteoconductive material comprises calcium and phosphorus. In some embodiments, the osteoconductive material comprises hydroxyapatite. In some embodiments, the osteoconductive material comprises collagen. In some embodiments, the osteoconductive material is in a particulate form.

Recent work has shown that plasmid DNA will not elicit an inflammatory response as does the use of viral vectors. Genes encoding bone (anabolic) agents such as BMP may be efficacious if injected into the uncoupled resorbing bone. In addition, overexpression of any of the growth factors provided herein or other agents which would limit local osteoclast activity would have positive effects on bone growth. In one embodiment, the plasmid contains the genetic code for human TGF-β or erythropoietin (EPO).

Accordingly, in some embodiments, the additional therapeutic agent is selected from the group consisting of viable cells and plasmid DNA.

We claim:

1. An inserter/expander instrument comprising:
   a) a first longitudinal member having a distal end portion adapted for engaging a first vertebral surface, an intermediate portion, and a proximal portion,
   b) a second longitudinal member having a distal end portion adapted for engaging a second vertebral surface, an intermediate portion, and a proximal portion,
   c) first and second cross bars distally pivotally attached to the longitudinal members at distal pivots; pivotally attached together at a third pivot; and slidably attached at their respective proximal ends to the opposing longitudinal member by a pin and groove arrangement,
   d) a first expansion actuation mechanism attached to the proximal portion of the first longitudinal member, the expansion actuation mechanism adapted to incrementally distally advance the proximal portion first cross bar to expand the distal portions of the longitudinal members, and
   e) a second expansion actuation mechanism attached to the proximal portion of the first longitudinal member, the second expansion actuation mechanism adapted to incrementally distally advance the proximal portion of the first cross bar to expand the distal portions of the longitudinal members,
   wherein the second expansion mechanism comprises a knob having a threaded shaft extending therefrom, the thread of the shaft mating with a thread upon an internal diameter of a tube located with the first longitudinal member, and
   wherein the shaft of the knob is connected to the pin of the pin and groove arrangement, so that distal movement of the shaft of the knob results in an opening of the cross bars.

2. The instrument of claim 1 wherein the first expansion mechanism comprises a pistol grip comprising a handle and lever pivotally attached to the handle.

3. The instrument of claim 2 wherein the lever is pivotally attached to a shaft located within the proximal portion of the first longitudinal member.

4. The instrument of claim 1 wherein the proximal portion of the first longitudinal member is cannulated.

* * * * *